(12) United States Patent
Pudil et al.

(10) Patent No.: US 12,285,552 B2
(45) Date of Patent: Apr. 29, 2025

(54) PRECISION DIALYSIS THERAPY BASED ON SORBENT EFFLUENT ANALYSIS

(71) Applicant: Mozarc Medical US LLC, Minneapolis, MN (US)

(72) Inventors: Bryant J. Pudil, Plymouth, MN (US); Christopher M. Hobot, Rogers, MN (US); Martin T. Gerber, Maple Grove, MN (US)

(73) Assignee: Mozarc Medical US LLC, Minneapolis, MN (US)

( * ) Notice: Subject to any disclaimer, the term of this patent is extended or adjusted under 35 U.S.C. 154(b) by 937 days.

(21) Appl. No.: 16/435,976

(22) Filed: Jun. 10, 2019

(65) Prior Publication Data
US 2020/0054807 A1   Feb. 20, 2020

Related U.S. Application Data

(60) Provisional application No. 62/718,460, filed on Aug. 14, 2018.

(51) Int. Cl.
*A61M 1/16*   (2006.01)

(52) U.S. Cl.
CPC ........ *A61M 1/1696* (2013.01); *A61M 1/1609* (2014.02); *A61M 2205/3334* (2013.01);
(Continued)

(58) Field of Classification Search
CPC .............. A61M 1/1609; A61M 1/1613; A61M 1/1696; A61M 2205/3334; A61M 2205/3368; A61M 2230/208; A61M 1/16; A61M 1/14; A61M 1/1656; A61M 1/28; A61M 1/1607; A61M 1/1611; A61M 1/1654; A61M 1/1692; A61M 1/1694; A61M 1/3486; A61M 2202/0225;
(Continued)

(56) References Cited

U.S. PATENT DOCUMENTS

| 1,617,288 A | 2/1927 | Kenney |
| 2,703,313 A | 1/1950 | Gill |

(Continued)

FOREIGN PATENT DOCUMENTS

| CN | 1487853 A | 4/2004 |
| CN | 102573618 | 7/2012 |

(Continued)

OTHER PUBLICATIONS

Rosenbaum et al, Prediction of hemodialysis sorbent cartridge urea nitrogen capacity and sodium release from in vitro tests, Nov. 2007, Hemodialysis International 2008;12:244-253, p. 1-10 (Year: 2007).*

(Continued)

*Primary Examiner* — Dirk R Bass

(57) ABSTRACT

The invention relates to devices, systems, and methods for preforming a precision dialysis therapy session based on an analysis of an effluent from a zirconium phosphate sorbent module during an ammonium removal process. The settings for the precision dialysis therapy session can be obtained by estimating a patient's physiological state, such as BUN level, based on the analysis of the effluent for a particular sorbent module linked to a particular patient.

22 Claims, 6 Drawing Sheets

(52) U.S. Cl.
CPC ............... *A61M 2205/3368* (2013.01); *A61M 2230/208* (2013.01)

(58) Field of Classification Search
CPC ........ A61M 2205/3303; A61M 1/1603; A61M 1/1605; A61M 1/1619; A61M 1/1635; A61M 1/165; A61M 1/1672; A61M 1/284; A61M 1/287; A61M 1/3406; A61M 1/342; A61M 1/3424; A61M 1/3455; A61M 1/3472; A61M 1/3482; A61M 1/3607; A61M 1/3609; A61M 1/3679; A61M 2202/0021; A61M 2202/049; A61M 2202/0498; A61M 2205/15; A61M 2205/18; A61M 2205/33; A61M 2205/3317; A61M 2205/3324; A61M 2205/502; A61M 2230/04; A61M 2230/20
See application file for complete search history.

(56) References Cited

U.S. PATENT DOCUMENTS

| | | |
|---|---|---|
| 3,608,729 A | 9/1971 | Haselden |
| 3,617,545 A | 11/1971 | Dubois |
| 3,617,558 A | 11/1971 | Jones |
| 3,669,878 A | 6/1972 | Marantz |
| 3,669,880 A | 6/1972 | Marantz |
| 3,776,819 A | 12/1973 | Williams |
| 3,840,835 A | 10/1974 | Kussy |
| 3,850,835 A | 11/1974 | Marantz |
| 3,884,808 A | 5/1975 | Scott |
| 3,902,490 A | 9/1975 | Jacobsen |
| 3,989,622 A | 11/1976 | Marantz |
| 4,060,485 A | 11/1977 | Eaton |
| 4,073,725 A | 2/1978 | Takeuchi |
| 4,094,775 A | 6/1978 | Mueller |
| 4,142,845 A | 3/1979 | Lepp |
| 4,192,748 A | 3/1980 | Hyden |
| 4,206,054 A | 6/1980 | Moore |
| 4,209,392 A | 6/1980 | Wallace |
| 4,269,708 A | 5/1981 | Bonomini |
| 4,371,385 A | 2/1983 | Johnson |
| 4,374,382 A | 2/1983 | Markowitz |
| 4,376,707 A | 3/1983 | Lehmann |
| 4,381,999 A | 5/1983 | Boucher |
| 4,460,555 A | 7/1984 | Thompson |
| 4,556,063 A | 12/1985 | Thompson |
| 4,562,751 A | 1/1986 | Nason |
| 4,581,141 A | 4/1986 | Ash |
| 4,612,122 A | 9/1986 | Ambrus |
| 4,650,587 A | 3/1987 | Polak |
| 4,661,246 A | 4/1987 | Ash |
| 4,678,408 A | 7/1987 | Mason |
| 4,684,460 A | 8/1987 | Issautier |
| 4,685,903 A | 8/1987 | Cable |
| 4,687,582 A | 8/1987 | Dixon |
| 4,750,494 A | 6/1988 | King |
| 4,765,907 A | 8/1988 | Scott |
| 4,826,663 A | 5/1989 | Alberti |
| 4,828,693 A | 5/1989 | Lindsay |
| 5,032,615 A | 7/1991 | Ward et al. |
| 5,047,014 A | 9/1991 | Mosebach et al. |
| 5,080,653 A | 1/1992 | Voss |
| 5,092,886 A | 3/1992 | Dobos-Hardy |
| 5,097,122 A | 3/1992 | Coiman |
| 5,127,404 A | 7/1992 | Wyborny |
| 5,192,132 A | 3/1993 | Pelensky |
| 5,230,702 A | 7/1993 | Lindsay |
| 5,284,470 A | 2/1994 | Beltz |
| 5,302,288 A | 4/1994 | Meidl |
| 5,305,745 A | 4/1994 | Zacouto |
| 5,308,315 A | 5/1994 | Khuri |
| 5,318,750 A | 6/1994 | Lascombes |
| 5,399,157 A | 3/1995 | Goux |
| 5,441,049 A | 8/1995 | Masano |
| 5,442,969 A | 8/1995 | Troutner |
| 5,445,610 A | 8/1995 | Evert |
| 5,468,388 A | 11/1995 | Goddard |
| 5,507,723 A | 4/1996 | Keshaviah |
| 5,662,806 A | 9/1997 | Keshaviah et al. |
| 5,683,432 A | 11/1997 | Goedeke |
| 5,685,988 A | 11/1997 | Malchesky |
| 5,716,400 A | 2/1998 | Davidson |
| 5,744,031 A | 4/1998 | Bene |
| 5,762,782 A | 6/1998 | Kenley |
| 5,770,086 A | 6/1998 | Indriksons |
| 5,849,179 A | 12/1998 | Emerson |
| 5,858,186 A | 1/1999 | Glass |
| 5,938,634 A | 8/1999 | Packard |
| 5,938,938 A | 8/1999 | Bosetto |
| 5,944,684 A | 8/1999 | Roberts |
| 6,036,858 A | 3/2000 | Carlsson |
| 6,048,732 A | 4/2000 | Anslyn |
| 6,052,622 A | 4/2000 | Holmstrom |
| 6,058,331 A | 5/2000 | King |
| 6,114,176 A | 9/2000 | Edgson et al. |
| 6,126,831 A | 10/2000 | Goldau |
| 6,171,480 B1 | 1/2001 | Lee |
| 6,230,059 B1 | 5/2001 | Duffin |
| 6,248,093 B1 | 6/2001 | Moberg |
| 6,254,567 B1 | 7/2001 | Treu |
| 6,321,101 B1 | 11/2001 | Holmstrom |
| 6,362,591 B1 | 3/2002 | Moberg |
| 6,363,279 B1 | 3/2002 | Ben-Haim |
| 6,390,969 B1 | 5/2002 | Bolling et al. |
| 6,491,993 B1 | 12/2002 | Forbes |
| 6,521,184 B1 | 2/2003 | Edgson et al. |
| 6,554,798 B1 | 4/2003 | Mann |
| 6,555,986 B2 | 4/2003 | Moberg |
| 6,565,525 B1 | 5/2003 | Burbank et al. |
| 6,572,769 B2 | 6/2003 | Rajan |
| 6,579,460 B1 | 6/2003 | Willis |
| 6,585,675 B1 | 7/2003 | O'Mahony et al. |
| 6,589,229 B1 | 7/2003 | Connelly |
| 6,593,747 B2 | 7/2003 | Puskas |
| 6,596,234 B1 | 7/2003 | Schnell et al. |
| 6,602,399 B1 | 8/2003 | Fromherz |
| 6,627,164 B1 | 9/2003 | Wong |
| 6,666,840 B1 | 12/2003 | Falkvall et al. |
| 6,676,608 B1 | 1/2004 | Keren |
| 6,695,807 B2 | 2/2004 | Bell et al. |
| 6,711,439 B1 | 3/2004 | Bradley |
| 6,719,745 B1 | 4/2004 | Taylor |
| 6,773,412 B2 | 8/2004 | O'Mahony et al. |
| 6,814,724 B2 | 11/2004 | Taylor |
| 6,818,196 B2 | 11/2004 | Wong |
| 6,861,266 B1 | 3/2005 | Sternby |
| 6,878,258 B2 | 4/2005 | Hughes |
| 6,878,283 B2 | 4/2005 | Thompson |
| 6,878,285 B2 | 4/2005 | Hughes |
| 6,890,315 B1 | 5/2005 | Levin |
| 6,923,782 B2 | 8/2005 | O'Mahony et al. |
| 6,960,179 B2 | 11/2005 | Gura |
| 7,029,456 B2 | 4/2006 | Ware et al. |
| 7,033,498 B2 | 4/2006 | Wong |
| 7,077,819 B1 | 7/2006 | Goldau |
| 7,097,630 B2 | 8/2006 | Gotch |
| 7,101,519 B2 | 9/2006 | Wong |
| 7,128,750 B1 | 10/2006 | Stergiopulos |
| 7,153,693 B2 | 12/2006 | Tajiri |
| 7,208,092 B2 | 4/2007 | Micheli |
| 7,241,272 B2 | 7/2007 | Karoor |
| 7,276,042 B2 | 10/2007 | Polaschegg |
| 7,309,323 B2 | 12/2007 | Gura |
| 7,318,892 B2 | 1/2008 | Connell |
| 7,326,576 B2 | 2/2008 | Womble et al. |
| 7,384,543 B2 | 6/2008 | Jonsson et al. |
| 7,435,342 B2 | 10/2008 | Tsukamoto |
| 7,462,161 B2 | 12/2008 | O'Mahony et al. |
| 7,488,447 B2 | 2/2009 | Sternby |
| 7,537,688 B2 | 5/2009 | Tarumi |
| 7,544,300 B2 | 6/2009 | Brugger |
| 7,544,737 B2 | 6/2009 | Poss |

(56) References Cited

U.S. PATENT DOCUMENTS

| | | |
|---|---|---|
| 7,563,240 B2 | 7/2009 | Gross |
| 7,566,432 B2 | 7/2009 | Wong |
| 7,575,564 B2 | 8/2009 | Childers |
| 7,597,806 B2 | 10/2009 | Uchi |
| 7,674,231 B2 | 3/2010 | McCombie |
| 7,674,237 B2 | 3/2010 | O'Mahony et al. |
| 7,686,778 B2 | 3/2010 | Burbank et al. |
| 7,704,361 B2 | 4/2010 | Garde |
| 7,736,507 B2 | 6/2010 | Wong |
| 7,754,852 B2 | 7/2010 | Burnett |
| 7,756,572 B1 | 7/2010 | Fard |
| 7,776,001 B2 | 8/2010 | Brugger et al. |
| 7,776,006 B2 | 8/2010 | Childers |
| 7,776,210 B2 | 8/2010 | Rosenbaum |
| 7,794,141 B2 | 9/2010 | Perry |
| 7,794,419 B2 | 9/2010 | Paolini |
| 7,850,635 B2 | 12/2010 | Polaschegg |
| 7,867,214 B2 | 1/2011 | Childers |
| 7,901,376 B2 | 3/2011 | Steck et al. |
| 7,905,853 B2 | 3/2011 | Chapman et al. |
| 7,922,686 B2 | 4/2011 | Childers |
| 7,922,911 B2 | 4/2011 | Micheli |
| 7,947,179 B2 | 5/2011 | Rosenbaum |
| 7,955,289 B2 | 6/2011 | O'Mahony et al. |
| 7,955,290 B2 | 6/2011 | Karoor |
| 7,967,022 B2 | 6/2011 | Grant |
| 7,981,082 B2 | 7/2011 | Wang |
| 7,988,854 B2 | 8/2011 | Tsukamoto |
| 8,002,726 B2 | 8/2011 | Karoor |
| 8,012,118 B2 | 9/2011 | Curtin |
| 8,029,454 B2 | 10/2011 | Kelly |
| 8,034,161 B2 | 10/2011 | Gura |
| 8,066,658 B2 | 11/2011 | Karoor |
| 8,070,709 B2 | 12/2011 | Childers |
| 8,080,161 B2 | 12/2011 | Ding et al. |
| 8,087,303 B2 | 1/2012 | Beavis |
| 8,096,969 B2 | 1/2012 | Roberts |
| 8,180,574 B2 | 5/2012 | Lo |
| 8,182,673 B2 | 5/2012 | Childers et al. |
| 8,183,046 B2 | 5/2012 | Lu |
| 8,187,250 B2 | 5/2012 | Roberts |
| 8,197,439 B2 | 6/2012 | Wang |
| 8,206,591 B2 | 6/2012 | Kotanko et al. |
| 8,211,048 B2 | 7/2012 | Szamosfalvi et al. |
| 8,221,529 B2 | 7/2012 | Childers et al. |
| 8,226,595 B2 | 7/2012 | Childers et al. |
| 8,246,826 B2 | 8/2012 | Wilt |
| 8,267,881 B2 | 9/2012 | O'Mahony et al. |
| 8,273,049 B2 | 9/2012 | Demers |
| 8,292,594 B2 | 10/2012 | Tracey |
| 8,303,532 B2 | 11/2012 | Hamada |
| 8,313,642 B2 | 11/2012 | Yu |
| 8,317,492 B2 | 11/2012 | Demers |
| 8,357,113 B2 | 1/2013 | Childers |
| 8,357,298 B2 | 1/2013 | Demers et al. |
| 8,366,316 B2 | 2/2013 | Kamen |
| 8,366,655 B2 | 2/2013 | Kamen |
| 8,376,999 B2 | 2/2013 | Busby et al. |
| 8,377,012 B2 | 2/2013 | Chapman et al. |
| 8,377,308 B2 | 2/2013 | Kreymann et al. |
| 8,388,567 B2 | 3/2013 | Rovatti |
| 8,404,491 B2 | 3/2013 | Li |
| 8,409,441 B2 | 4/2013 | Wilt |
| 8,409,444 B2 | 4/2013 | Wong |
| 8,449,487 B2 | 5/2013 | Hovland et al. |
| 8,480,607 B2 | 7/2013 | Davies |
| 8,499,780 B2 | 8/2013 | Wilt |
| 8,518,260 B2 | 8/2013 | Raimann |
| 8,535,525 B2 | 9/2013 | Heyes |
| 8,580,112 B2 | 11/2013 | Updyke |
| 8,597,227 B2 | 12/2013 | Childers |
| 8,647,506 B2 | 2/2014 | Wong |
| 8,696,626 B2 | 4/2014 | Kirsch |
| 8,733,559 B2 | 5/2014 | Wong |
| 8,764,981 B2 | 7/2014 | Ding |
| 8,777,892 B2 | 7/2014 | Sandford |
| 8,903,492 B2 | 12/2014 | Soykan |
| 9,144,640 B2 | 9/2015 | Pudil |
| 9,254,355 B2 | 2/2016 | Sandford |
| 9,527,015 B2 | 12/2016 | Chau |
| 2001/0007931 A1 | 7/2001 | Blatter |
| 2001/0009756 A1 | 7/2001 | Hei et al. |
| 2002/0016550 A1 | 2/2002 | Sweeney |
| 2002/0027106 A1 | 3/2002 | Smith |
| 2002/0042561 A1 | 4/2002 | Schulman |
| 2002/0062098 A1 | 5/2002 | Cavicchioli et al. |
| 2002/0112609 A1 | 8/2002 | Wong |
| 2002/0117436 A1 | 8/2002 | Rajan |
| 2003/0080059 A1 | 5/2003 | Peterson |
| 2003/0097086 A1 | 5/2003 | Gura |
| 2003/0105435 A1 | 6/2003 | Taylor |
| 2003/0113931 A1 | 6/2003 | Pan |
| 2003/0114787 A1 | 6/2003 | Gura |
| 2003/0138348 A1 | 7/2003 | Bell et al. |
| 2003/0187479 A1 | 10/2003 | Thong |
| 2004/0019312 A1 | 1/2004 | Childers |
| 2004/0019320 A1 | 1/2004 | Childers |
| 2004/0030277 A1 | 2/2004 | O'Mahony et al. |
| 2004/0037986 A1 | 2/2004 | Houston et al. |
| 2004/0054315 A1 | 3/2004 | Levin et al. |
| 2004/0082903 A1 | 4/2004 | Micheli |
| 2004/0084358 A1 | 5/2004 | O'Mahony et al. |
| 2004/0099593 A1 | 5/2004 | DePaolis |
| 2004/0147900 A1 | 7/2004 | Polaschegg |
| 2004/0168963 A1 | 9/2004 | King |
| 2004/0215090 A1 | 10/2004 | Erkkila |
| 2004/0257409 A1 | 12/2004 | Cheok |
| 2005/0006296 A1 | 1/2005 | Sullivan |
| 2005/0056592 A1 | 3/2005 | Braunger |
| 2005/0065760 A1 | 3/2005 | Murtfeldt |
| 2005/0101901 A1 | 5/2005 | Gura |
| 2005/0113796 A1 | 5/2005 | Taylor |
| 2005/0126961 A1 | 6/2005 | Bissler |
| 2005/0131332 A1 | 6/2005 | Kelly |
| 2005/0126998 A1 | 7/2005 | Childers |
| 2005/0148923 A1 | 7/2005 | Sternby |
| 2005/0150832 A1 | 7/2005 | Tsukamoto |
| 2005/0230313 A1 | 10/2005 | O'Mahony et al. |
| 2005/0234354 A1 | 10/2005 | Rowlandson |
| 2005/0234381 A1 | 10/2005 | Niemetz |
| 2005/0274658 A1 | 12/2005 | Rosenbaum |
| 2006/0025661 A1 | 2/2006 | Sweeney |
| 2006/0037483 A1 | 2/2006 | Kief |
| 2006/0217771 A1 | 2/2006 | Soykan |
| 2006/0157413 A1 | 7/2006 | Bene |
| 2006/0189926 A1 | 8/2006 | Hall et al. |
| 2006/0195064 A1 | 8/2006 | Plahey |
| 2006/0226079 A1 | 10/2006 | Mori |
| 2006/0241543 A1 | 10/2006 | Gura |
| 2006/0241709 A1 | 10/2006 | Soykan |
| 2006/0264894 A1 | 11/2006 | Moberg |
| 2007/0007208 A1 | 1/2007 | Brugger |
| 2007/0055296 A1 | 3/2007 | Stergiopulos |
| 2007/0066928 A1 | 3/2007 | Lannoy |
| 2007/0138011 A1 | 6/2007 | Hofmann |
| 2007/0175827 A1 | 8/2007 | Wariar |
| 2007/0179431 A1 | 8/2007 | Roberts |
| 2007/0213665 A1 | 9/2007 | Curtin |
| 2007/0215545 A1 | 9/2007 | Bissler |
| 2007/0243113 A1 | 10/2007 | DiLeo |
| 2007/0255250 A1 | 11/2007 | Moberg |
| 2008/0006570 A1 | 1/2008 | Gura |
| 2008/0011664 A1 | 1/2008 | Karoor |
| 2008/0015493 A1 | 1/2008 | Childers et al. |
| 2008/0021337 A1 | 1/2008 | Li |
| 2008/0051696 A1 | 2/2008 | Curtin |
| 2008/0053905 A9 | 3/2008 | Brugger |
| 2008/0067132 A1 | 3/2008 | Ross |
| 2008/0215247 A1 | 9/2008 | Tonelli |
| 2008/0217245 A1 | 9/2008 | Rambod |
| 2008/0241031 A1 | 10/2008 | Li |
| 2008/0292935 A1 | 11/2008 | Roelofs |
| 2009/0020471 A1 | 1/2009 | Tsukamoto |
| 2009/0078636 A1 | 3/2009 | Uchi |

(56) References Cited

U.S. PATENT DOCUMENTS

| | | |
|---|---|---|
| 2009/0084199 A1 | 4/2009 | Wright |
| 2009/0101552 A1 | 4/2009 | Fulkerson |
| 2009/0101577 A1 | 4/2009 | Fulkerson |
| 2009/0120864 A1 | 5/2009 | Fulkerson |
| 2009/0127193 A1 | 5/2009 | Updyke |
| 2009/0149795 A1 | 6/2009 | O'Mahony et al. |
| 2009/0216045 A1 | 8/2009 | Singh |
| 2009/0266358 A1 | 10/2009 | Sacristan Rock |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2010/0004588 A1 | 1/2010 | Yeh |
| 2010/0007838 A1 | 1/2010 | Fujimoto |
| 2010/0010429 A1 | 1/2010 | Childers |
| 2010/0018923 A1 | 1/2010 | Rohde et al. |
| 2010/0030151 A1 | 2/2010 | Kirsch |
| 2010/0051529 A1 | 3/2010 | Grant et al. |
| 2010/0051552 A1 | 3/2010 | Rohde |
| 2010/0076364 A1 | 3/2010 | O'Mahony et al. |
| 2010/0078381 A1 | 4/2010 | Merchant |
| 2010/0078387 A1 | 4/2010 | Wong |
| 2010/0084330 A1 | 4/2010 | Wong |
| 2010/0094158 A1 | 4/2010 | Solem |
| 2010/0100027 A1 | 4/2010 | Schilthuizen |
| 2010/0101195 A1 | 4/2010 | Clements |
| 2010/0102190 A1 | 4/2010 | Zhu et al. |
| 2010/0114001 A1 | 5/2010 | O'Mahony et al. |
| 2010/0114012 A1 | 5/2010 | Sandford |
| 2010/0137693 A1 | 6/2010 | Porras |
| 2010/0168546 A1 | 7/2010 | Kamath |
| 2010/0168641 A1 | 7/2010 | O'Mahony et al. |
| 2010/0213127 A1 | 8/2010 | Castellarnau |
| 2010/0217181 A1 | 8/2010 | Roberts |
| 2010/0224492 A1 | 9/2010 | Ding |
| 2010/0234795 A1 | 9/2010 | Wallenas |
| 2010/0241045 A1 | 9/2010 | Kelly |
| 2010/0252490 A1 | 10/2010 | Fulkerson |
| 2010/0312172 A1 | 12/2010 | Hoffman |
| 2010/0312174 A1 | 12/2010 | Hoffman |
| 2010/0314314 A1 | 12/2010 | Ding |
| 2010/0326911 A1 | 12/2010 | Rosenbaum |
| 2011/0009798 A1 | 1/2011 | Kelly |
| 2011/0017665 A1 | 1/2011 | Updyke |
| 2011/0048949 A1 | 3/2011 | Ding et al. |
| 2011/0066043 A1 | 3/2011 | Banet |
| 2011/0077574 A1 | 3/2011 | Sigg |
| 2011/0079558 A1 | 4/2011 | Raimann |
| 2011/0087187 A1 | 4/2011 | Beck |
| 2011/0130666 A1 | 6/2011 | Dong |
| 2011/0163034 A1 | 7/2011 | Castellarnau |
| 2011/0171713 A1 | 7/2011 | Bluchel |
| 2011/0184340 A1 | 7/2011 | Tan |
| 2011/0220562 A1 | 9/2011 | Beiriger |
| 2011/0247973 A1 | 10/2011 | Sargand |
| 2011/0272337 A1 | 11/2011 | Palmer |
| 2011/0272352 A1 | 11/2011 | Braig |
| 2011/0297593 A1 | 12/2011 | Kelly |
| 2011/0315611 A1 | 12/2011 | Fulkerson |
| 2011/0315632 A1 | 12/2011 | Freije |
| 2012/0016228 A1 | 1/2012 | Kroh |
| 2012/0018377 A1 | 1/2012 | Tsukamoto |
| 2012/0083729 A1 | 4/2012 | Childers |
| 2012/0085707 A1 | 4/2012 | Beiriger |
| 2012/0092025 A1 | 4/2012 | Volker |
| 2012/0095402 A1 | 4/2012 | Lande |
| 2012/0115248 A1 | 5/2012 | Ansyln |
| 2012/0220528 A1 | 8/2012 | VanAntwerp |
| 2012/0248017 A1 | 10/2012 | Beiriger |
| 2012/0258545 A1 | 10/2012 | Ash |
| 2012/0258546 A1 | 10/2012 | Marran |
| 2012/0273354 A1 | 11/2012 | Orhan et al. |
| 2012/0273415 A1 | 11/2012 | Gerber |
| 2012/0273420 A1 | 11/2012 | Gerber |
| 2012/0277546 A1 | 11/2012 | Soykan |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2012/0303079 A1 | 11/2012 | Mahajan |
| 2013/0006128 A1 | 1/2013 | Olde et al. |
| 2013/0018095 A1 | 1/2013 | Vath |
| 2013/0019179 A1 | 1/2013 | Zhao |
| 2013/0020237 A1 | 1/2013 | Wilt et al. |
| 2013/0023812 A1 | 1/2013 | Hasegawa et al. |
| 2013/0025357 A1 | 1/2013 | Noack et al. |
| 2013/0027214 A1 | 1/2013 | Eng |
| 2013/0028809 A1 | 1/2013 | Barton |
| 2013/0030347 A1 | 1/2013 | Sugioka |
| 2013/0030348 A1 | 1/2013 | Lauer |
| 2013/0030356 A1 | 1/2013 | Ding |
| 2013/0037142 A1 | 2/2013 | Farrell |
| 2013/0037465 A1 | 2/2013 | Heyes |
| 2013/0056418 A1 | 3/2013 | Kopperschmidt et al. |
| 2013/0072895 A1 | 3/2013 | Kreischer et al. |
| 2013/0075314 A1 | 3/2013 | Nikolic |
| 2013/0087210 A1 | 4/2013 | Brandl et al. |
| 2013/0110028 A1 | 5/2013 | Bachmann et al. |
| 2013/0116578 A1 | 5/2013 | An |
| 2013/0199998 A1 | 8/2013 | Kelly |
| 2013/0213890 A1 | 8/2013 | Kelly |
| 2013/0213891 A1 | 8/2013 | Karoor |
| 2013/0228516 A1 | 9/2013 | Jonsson |
| 2013/0274642 A1 | 10/2013 | Soykan |
| 2013/0324915 A1 | 12/2013 | (Krensky)Britton |
| 2013/0330208 A1 | 12/2013 | Ly |
| 2013/0331774 A1 | 12/2013 | Farrell |
| 2014/0001112 A1 | 1/2014 | Karoor |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1 | 3/2014 | Soykan |
| 2014/0110340 A1 | 4/2014 | White |
| 2014/0110341 A1 | 4/2014 | White |
| 2014/0138294 A1 | 5/2014 | Fulkerson |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0190885 A1 | 7/2014 | Meyer |
| 2014/0190886 A1* | 7/2014 | Pudil ............... A61M 1/1696 210/93 |
| 2014/0190891 A1 | 7/2014 | Lura |
| 2014/0217028 A1 | 8/2014 | Pudil |
| 2014/0217030 A1 | 8/2014 | Meyer |
| 2014/0220699 A1 | 8/2014 | Pudil |
| 2014/0251908 A1 | 9/2014 | Ding |
| 2014/0326671 A1 | 11/2014 | Kelly |
| 2014/0336568 A1 | 11/2014 | Wong |
| 2015/0057602 A1 | 2/2015 | Mason |
| 2015/0108069 A1 | 4/2015 | Merchant |
| 2015/0108609 A1 | 4/2015 | Kushida |
| 2015/0114891 A1 | 4/2015 | Meyer |
| 2015/0144539 A1 | 5/2015 | Pudil |
| 2015/0144542 A1 | 5/2015 | Pudil |
| 2015/0157960 A1 | 6/2015 | Pudil |
| 2015/0238673 A1 | 8/2015 | Gerber |
| 2015/0250937 A1 | 9/2015 | Pudil |
| 2015/0251161 A1 | 9/2015 | Pudil |
| 2015/0251162 A1 | 9/2015 | Pudil |
| 2015/0258266 A1 | 9/2015 | Merchant |
| 2015/0306292 A1 | 10/2015 | Pudil |
| 2015/0367051 A1* | 12/2015 | Gerber ............... A61M 1/1696 210/209 |
| 2015/0367052 A1 | 12/2015 | Gerber |
| 2015/0367055 A1* | 12/2015 | Pudil ............... A61M 1/1696 423/306 |
| 2015/0367056 A1 | 12/2015 | Gerber |
| 2015/0367057 A1 | 12/2015 | Gerber |
| 2015/0367058 A1 | 12/2015 | Gerber |
| 2015/0367059 A1 | 12/2015 | Gerber |
| 2015/0367060 A1 | 12/2015 | Gerber |
| 2016/0236188 A1 | 8/2016 | Menon |

(56) References Cited

U.S. PATENT DOCUMENTS

| | | | |
|---|---|---|---|
| 2016/0243299 | A1 | 8/2016 | Gerber |
| 2016/0243540 | A1 | 8/2016 | Menon |
| 2016/0243541 | A1 | 8/2016 | Menon |
| 2017/0087533 | A1* | 3/2017 | Hobot ............... B01J 39/09 |
| 2018/0221554 | A1* | 8/2018 | Mazack ........... A61M 1/1607 |
| 2018/0221852 | A1 | 8/2018 | Pudil |
| 2020/0054807 | A1* | 2/2020 | Pudil ............... A61M 1/1613 |

FOREIGN PATENT DOCUMENTS

| | | |
|---|---|---|
| CN | 102762268 | 10/2012 |
| CN | 103402563 A | 11/2013 |
| CN | 104936633 | 9/2015 |
| CN | 105992599 | 5/2016 |
| CN | 105658326 A | 6/2016 |
| CN | 106413878 A | 2/2017 |
| CN | 106535953 A | 3/2017 |
| DE | 3110128 A1 | 9/1982 |
| DE | 102011052188 | 1/2013 |
| EP | 266795 A2 | 11/1987 |
| EP | 0264695 | 4/1988 |
| EP | 0614081 A1 | 10/1993 |
| EP | 0614081 B1 | 7/2000 |
| EP | 711182 B1 | 6/2003 |
| EP | 1364666 A1 | 11/2003 |
| EP | 0906768 B1 | 2/2004 |
| EP | 1701752 A2 | 9/2006 |
| EP | 1450879 | 10/2008 |
| EP | 1991289 | 11/2008 |
| EP | 1592494 B1 | 6/2009 |
| EP | 2100553 A1 | 9/2009 |
| EP | 2575827 A2 | 12/2010 |
| EP | 2576453 A2 | 12/2011 |
| EP | 2446908 | 5/2012 |
| EP | 2701580 | 11/2012 |
| EP | 2701595 | 11/2012 |
| EP | 1545652 B1 | 1/2013 |
| EP | 1684625 B1 | 1/2013 |
| EP | 2142234 B1 | 1/2013 |
| EP | 2550984 A1 | 1/2013 |
| EP | 1345856 B1 | 3/2013 |
| EP | 1938849 B1 | 3/2013 |
| EP | 2219703 B1 | 3/2013 |
| EP | 2564884 A1 | 3/2013 |
| EP | 2564885 A1 | 3/2013 |
| EP | 2344220 B1 | 4/2013 |
| EP | 1345687 | 6/2013 |
| EP | 2701596 | 3/2014 |
| EP | 2950836 | 12/2015 |
| EP | 3546042 | 10/2019 |
| EP | 3626280 | 3/2020 |
| JP | S5070281 A | 6/1975 |
| JP | S51-55193 | 5/1976 |
| JP | S51-131393 | 11/1976 |
| JP | S61164562 | 7/1986 |
| JP | 2981573 | 11/1999 |
| JP | 2005511250 | 4/2005 |
| JP | H4-90963 | 5/2005 |
| JP | 200744602 | 2/2007 |
| JP | 200744602 A | 2/2007 |
| JP | 5099464 | 10/2012 |
| JP | 2013502987 | 10/2013 |
| WO | 9106326 A1 | 5/1991 |
| WO | 9532010 A1 | 11/1995 |
| WO | 9937342 | 7/1999 |
| WO | 2000038591 A2 | 7/2000 |
| WO | 0057935 | 10/2000 |
| WO | 200066197 A1 | 11/2000 |
| WO | 200170307 A1 | 9/2001 |
| WO | 2001085295 A2 | 9/2001 |
| WO | 0185295 A2 | 11/2001 |
| WO | 2002043859 | 6/2002 |
| WO | 2003043677 A2 | 5/2003 |
| WO | 2003043680 | 5/2003 |
| WO | WO 2003041764 | 5/2003 |
| WO | 2003051422 A2 | 6/2003 |
| WO | 2004008826 | 1/2004 |
| WO | 2004009156 | 1/2004 |
| WO | 2004030716 A2 | 4/2004 |
| WO | 2004030717 A2 | 4/2004 |
| WO | 2004064616 A2 | 8/2004 |
| WO | 2004062710 A3 | 10/2004 |
| WO | WO 2005/062973 A3 | 7/2005 |
| WO | 2005123230 | 12/2005 |
| WO | 2005123230 A2 | 12/2005 |
| WO | 2007089855 A2 | 8/2007 |
| WO | WO 20070103411 | 9/2007 |
| WO | 2008075951 A1 | 6/2008 |
| WO | 2009026603 | 12/2008 |
| WO | 2009026603 A1 | 3/2009 |
| WO | 2009064984 | 5/2009 |
| WO | 2009157877 A1 | 12/2009 |
| WO | 2009157878 A1 | 12/2009 |
| WO | 20090157877 | 12/2009 |
| WO | 2010028860 | 3/2010 |
| WO | 2010028860 A1 | 3/2010 |
| WO | 2010102190 A4 | 11/2010 |
| WO | 2010141949 | 12/2010 |
| WO | WO 2011/017215 | 2/2011 |
| WO | 2011025705 A1 | 3/2011 |
| WO | 2012148781 | 11/2012 |
| WO | 2012148786 | 11/2012 |
| WO | 2012148789 | 11/2012 |
| WO | 2012162515 A2 | 11/2012 |
| WO | 20120277551 | 11/2012 |
| WO | 2012172398 | 12/2012 |
| WO | 2013019179 | 2/2013 |
| WO | 2013019179 A1 | 2/2013 |
| WO | 2013019994 A2 | 2/2013 |
| WO | 2013022024 A1 | 2/2013 |
| WO | 2013022837 A1 | 2/2013 |
| WO | 2013025844 | 2/2013 |
| WO | 2013025957 | 2/2013 |
| WO | 2013027214 | 2/2013 |
| WO | 2013028809 | 2/2013 |
| WO | 2013028809 A3 | 2/2013 |
| WO | WO 2013/019994 | 2/2013 |
| WO | WO2014121238 A1 | 2/2013 |
| WO | 2013030642 A1 | 3/2013 |
| WO | 2013030643 A1 | 3/2013 |
| WO | 2013019994 A3 | 4/2013 |
| WO | 2012060700 | 5/2013 |
| WO | 2012162515 A3 | 5/2013 |
| WO | 2013025844 A3 | 5/2013 |
| WO | 2013101888 | 7/2013 |
| WO | 2013103607 A1 | 7/2013 |
| WO | 2013103906 | 7/2013 |
| WO | WO 2013/103607 | 7/2013 |
| WO | WO 2013109922 | 7/2013 |
| WO | 2013114063 A1 | 8/2013 |
| WO | 2013121162 A1 | 8/2013 |
| WO | 14066254 | 5/2014 |
| WO | 14066255 | 5/2014 |
| WO | 14077082 | 5/2014 |
| WO | 2014121162 | 8/2014 |
| WO | 2014121163 | 8/2014 |
| WO | 2014121167 | 8/2014 |
| WO | 2014121169 | 8/2014 |
| WO | 2015060914 | 4/2015 |
| WO | WO 2015/080895 | 4/2015 |
| WO | WO 2015/126879 | 8/2015 |
| WO | 2015142624 | 9/2015 |
| WO | 2015199764 | 12/2015 |
| WO | 2015199765 | 12/2015 |
| WO | 2015199863 | 12/2015 |
| WO | 2015199864 | 12/2015 |
| WO | WO 2016/191039 | 12/2016 |
| WO | WO 2016/191041 | 12/2016 |

OTHER PUBLICATIONS

Chinese Office Action for App. No. 201711179528.X, dated Jul. 27, 2020.

(56) References Cited

OTHER PUBLICATIONS

European Search Report for App. No. 20158130.3, dated Jul. 8, 2020.
European Search Report for App. No. 20164524.9, dated Aug. 21, 2020.
Chinese Office Action for App. No. 201810580243.5, dated Jul. 3, 2020.
U.S. Appl. No. 13/100,847, filed Nov. 10, 2011, C-Tech BioMedical Inc.
U.S. Appl. No. 13/565,733, filed Aug. 2, 2012, Medtronic.
U.S. Appl. No. 13/757,693, filed Feb. 1, 2013, Medtronic.
U.S. Appl. No. 13/757,709, filed Feb. 1, 2013, Medtronic.
U.S. Appl. No. 13/757,728, filed Feb. 1, 2013, Medtronic.
U.S. Appl. No. 13/836,538, filed Mar. 15, 2013, Medtronic.
U.S. Appl. No. 61/760,033, filed Feb. 1, 2012, Medtronic.
U.S. Appl. No. 14/637,606_OA.
U.S. Appl. No. 14/645,394_OA.
[NPL105] Brynda, et. al., The detection of toman 2-microglebuiin by grating coupler immunosensor with three dimensional antibody networks. Biosensors & Bioelectronics, 1999, 363-368, 14(4).
[NPL10] Wheaton, et al., Dowex Ion Exchange Resins-Fundamentals of Ion Exchange; Jun. 2000, pp. 1-9. http://www.dow.com/scripts/litorder.asp?filepath=liquidseps/pdfs/noreg/177-01837.pdf.
[NPL111] Zhong, et al., Miniature urea sensor based on H(+)-ion sensitive field effect transistor and its application in clinical analysis, Chin. J. Biotechnol., 1992, 57-65. 8(1).
[NPL119] PCT/US2012/034331, International Search Report and Written Opinion dated Jul. 9, 2012.
[NPL121] Roberts M, The regenerative dialysis (REDY) sorbent system. Nephrology, 1998, 275-278:4.
[NPL138] U.S. Appl. No. 61/480,544.
[NPL139] U.S. Appl. No. 61/480,541 dated Apr. 29, 2011.
[NPL142] Hemametrics, Crit-Line Hematocrit Accuracy, 2003, 1-5, vol. 1, Tech Note No. 11 (Rev. D).
[NPL144] Weissman, S., et al., Hydroxyurea-induced hepatitis in human immunodeficiency virus-positive patients. Clin. Infec. Dis, (Jul. 29, 1999): 223-224.
[NPL146] PCT/US2012/034334, International Search Report, Jul. 6, 2012.
[NPL147] PCT/US2012/034335, International Search Report, Sep. 5, 2012.
[NPL148] PCT/US/2012/034327, International Search Report, Aug. 13, 2013.
[NPL149] PCT/US/2012/034329, International Search Report, Dec. 3, 2012.
[NPL162] International Search Report from PCT/US2012/051946 mailed Mar. 4, 2013.
[NPL163] U.S. Appl. No. 61/526,209.
[NPL169] Wang, Fundamentals of intrathoracic impedance monitoring in heart failure, Am. J. Cardiology, 2007, 3G-10G: Suppl.
[NPL16] PCT/US2014/067650 International Search Report Written Opinion mailed Mar. 9, 2015.
[NPL176] Bleyer, et. al., Sudden and cardiac death rated in hemodialysis patients, Kidney International. 1999, 1553-1559: 55.
[NPL187] PCT/US2012/034333, International Preliminary Report on Patentability, Oct. 29, 2013.
[NPL188] PCT/US2012/034333, International Search Report, Aug. 29, 2012.
[NPL188] PCT/US2012/034333, International Search Report, Aug. 29, 2013.
[NPL197] PCT/US2012/034330, International Preliminary Report on Patentability, Oct. 29, 2013.
[NPL1] PCT/US2014/065950 International Search Report and Written Opinion mailed Feb. 24, 2015.
[NPL205] Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.
[NPL217] U.S. Appl. No. 13/757,722, filed Feb. 1, 2013.

[NPL218] U.S. Appl. No. 13/757,794, filed Feb. 2, 2012.
[NPL219] U.S. Appl. No. 13/791,755, filed Mar. 8, 2013.
[NPL21] U.S. Appl. No. 13/424,479 dated Nov. 1, 2012.
[NPL220] U.S. Appl. No. 13/757,792, filed Feb. 2, 2013.
[NPL222] U.S. Appl. No. 13/757,794, filed Feb. 2, 2013.
[NPL227] U.S. Appl. No. 13/837,287, filed Mar. 15, 2013.
[NPL22] U.S. Appl. No. 13/424,429 dated Nov. 1, 2012.
[NPL230] Redfield, et. al., Restoration of renal response to atria! natriuretic factor in experimental low-output heat failure, Am. J. Physiol., Oct. 1, 1989, R917-923:257.
[NPL231] Rogoza, et. al., Validation of A&D UA-767 device for the self-measurement of blood pressure, Blood Pressure Monitoring, 2000, 227-231, 5(4).
[NPL234] Lima, et al., An electrochemical sensor based on nanostructure hollandite-type manganese oxide for detection of potassium ion, Sensors, Aug. 24, 2009, 6613-8625, 9.
[NPL235] Maclean, Et, Al., Effects of hindlimb contraction on pressor and muscle interstitial metabolite responses in the cat, J. App. Physiol., 1998, 1583-1592, 85(4).
[NPL237] U.S. Appl. No. 13/757,693, dated Feb. 1, 2013.
[NPL238] PCT Application, PCT/US20013/020404, filed Jan. 4, 2013.
[NPL23] U.S. Appl. No. 13/424,525.
[NPL240] U.S. Appl. No. 13/836,973, filed Mar. 15, 2013.
[NPL241] U.S. Appl. No. 14/259,655, filed Apr. 23, 2014.
[NPL242] U.S. Appl. No. 14/259,589, filed Apr. 23, 2014.
[NPL243] U.S. Appl. No. 13/757,693, filed Jan. 4, 2013.
[NPL244] U.S. Appl. No. 13/836,079, filed Mar. 15, 2013.
[NPL245] U.S. Appl. No. 14/240,129, filed Aug. 22, 2013.
[NPL246] PCT/US2014/014346 International Search Report and Written Opinion.
[NPL247] U.S. Appl. No. 13/835,735, filed Mar. 15, 2013.
[NPL248] PCT/US2014/014345 International Search Report and Written Opinion, mailed May 2014.
[NPL250] U.S. Appl. No. 13/835,735 IDS, filed Jun. 13, 2013.
[NPL264] PCT/US2014/014357 International Search Report and Written Opinion dated May 19, 2014.
[NPL264] PCT/US2014/014357 International Search Report and Written Opinion mailed May 19, 2014.
[NPL268] Ronco et al. 2008, Cardiorenal Syndrome, Journal American College Cardiology, 52:1527-1539, ABSTRACT.
[NPL26] Overgaard, et. al., Activity-induced recovery of excitability in K+-depressed rat soleus muscle, Am. J. P 280: R48-R55, Jan. 1, 2001.
[NPL27] Overgaard et. al., Relations between excitability and contractility in rate soleusmuscle: role of the NA+-K+ pump and NA+-K-S gradients. Journal of Physiology, 1999, 215-225, 518(1).
[NPL2] PCT/US2015/032492 International Search Report mailed Nov. 19, 2015.
[NPL306] Coast, et al. 1990, An approach to Cardiac Arrhythmia analysis Using Hidden Markov Models, IEEE Transactions On Biomedical Engineering. 1990, 37(9):826-835.
[NPL310] U.S. Appl. No. 61/480,532.
[NPL317] U.S. Appl. No. 61/480,530.
[NPL318] U.S. Appl. No. 61/480,528 dated Apr. 29, 2011.
[NPL32] Secemsky, et. al., High prevalence of cardiac autonomic dysfunction and T-wave alternans in dialysis patients. Heart Rhythm, Apr. 2011, 592-598 : vol. 8, No. 4.
[NPL35] Wei, et. al., Fullerene-cryptand coated piezoelectric crystal urea sensor based on urease, Analytica Chimica Acta, 2001,77-85:437.
[NPL376] Gambro AK 96 Dialysis Machine Operators Manual, Dec. 2012. p. 1-140.
[NPL376] Gambro AK 96 Dialysis Machine Operators Manual, Dec. 2012. p. 141-280.
[NPL376] Gambro AK 96 Dialysis Machine Operators Manual, Dec. 2012. p. 281-420.
[NPL376] Gambro AK 96 Dialysis Machine Operators Manual, Dec. 2012. p. 421-534.
[NPL37] U.S. Appl. No. 13/368,225 dated Feb. 7, 2012.
[NPL383] Leifer et al., A Study on the Temperature Variation of Rise Velocity for Large Clean Bubbles, J. Atmospheric & Oceanic Tech., vol. 17, pp. 1392-1402, Oct. 2000.

(56) References Cited

OTHER PUBLICATIONS

[NPL384] Talaia, Terminal Velocity of a Bubble Rise in a Liquid Column, World Acad. of Sci., Engineering & Tech., vol. 28, pp. 264-268, Published Jan. 1, 2007.
[NPL386] The FHN Trial Group. In-Center. Hemodialysis Six Times per Week versus Three Times per Week, New England Journal of Medicine, 2010 ABSTRACT.
[NPL387] Gotch FA, Sargent JA A mechanistic analysis of the National Cooperative Dialysis Study (NCDS). Kidney int. 1985: 28:526-34.
[NPL388] Daugirdas JT. Second generation logarithmic estimates of single-pool variable vol. Kt/V and analysis of error. J Am Soc Nephrol, 1993: 4:1205-13.
[NPL389] Steil et al. Intl Journ Artif Organs, 1993, In Vivo Verification of an Automatic Noninvasive System for Real Time Kt Evaluation, Asaio J., 1993, 39:M348-52.
[NPL39] PCT/US2012/034332, International Search Report, Jul. 5, 2012.
[NPL3] PCT/US2015/019901 International Search Report and Written Opinion mailed Jun. 5, 2015.
[NPL46] Siegenthaler, et al., Pulmonary fluid status monitoring with intrathoracic impedance, Journal of Clinical Monitoring and Computing, 24:449-451, published Jan. 12, 2011.
[NPL47] U.S. Appl. No. 61/480,544.
[NPL494] John Wm Agar: Review: Understanding sorbent dialysis systems, NEPHROLOGY, vol. 15, No. 4, Jun. 1, 2010, pp. 406-411.
[NPL499] Ep. App. 14746193.3 Search Report dated Oct. 19, 2016.
[NPL4] PCT/US2015/016270 International Search Report and Written Opinion mailed Jun. 5, 2015.
[NPL518] Office Action in U.S. Appl. No. 14/269,589, Dated Nov. 4, 2016.
[NPL519] Office Action in U.S. Appl. No. 13/586,824 Dated Dec. 21, 2015.
[NPL520] Office Action in U.S. Appl. No. 13/586,824 Dated Jun. 4, 2015.
[NPL532] Eureopean Search Report for App. No. EP14745643 Dated Oct. 6, 2016.
[NPL534] Office Action in U.S. Appl. No. 13/586,824 Dated Dec. 21, 2015.
[NPL548] PCT/US15/18587 International Preliminary Report on Patentability Dated Jun. 6, 2016.
[NPL550] European Search Opinion for App. No. EP12826180 Dated Mar. 19, 2015.
[NPL551] European Search Opinion for App. No. EP12826180 Dated Jan. 18, 2016.
[NPL552] Khanna, Ramesh, R.T. Krediet, and Karl D. Nolph. Nolph and Gokals Textbook of Peritoneal Dialysis.New York: Springer 2009. Print.
[NPL553] Ruperez et al., Comparison of a tubular pulsatile pump and a volumetric pump for continuous venovenous renal replacement therapy in a pediatric animal model, 51 Asaio J. 372, 372-375 (2005).
[NPL554] St. Peter et al., Liver and kidney preservation by perfusion, 359 The Lancet 604, 606(2002).
[NPL555] Dasselaar et al., Measurement of relative blood volume changes during hemodialysis: merits and limitations, 20 Nephrol Dial Transpl. 2043, 2043-2044 (2005).
[NPL556] Ralph T. Yang, Adsorbents: Fundamentals and Applications 109 (2003).
[NPL557] Henny H. Billett, Hemoglobin and Hematocrit, in Clinical Methods: The History, Physical, and Laboratory Examinations 719(HK Walker, WD Hall, & JW Hurst ed., 1990).
[NPL558] Office Action in App. No. 13/565, 733 Dated Jan. 11, 2016.
[NPL559] Office Action in App. No. 13/565, 733 Dated Jun. 11, 2015.
[NPL55] U.S. Appl. No. 13/424,454.
[NPL560] Office Action in U.S. Appl. No. 13/586,824 Dated Jun. 4, 2015.
[NPL561] Office Action in U.S. Appl. No. 13/757,792 Dated Jun. 2, 2016.
[NPL562] Office Action in U.S. Appl. No. 13/757,796 Dated Apr. 13, 2015.
[NPL563] Office Action in U.S. Appl. No. 13/757,796 Dated Dec. 21, 2015.
[NPL564] Office Action in U.S. Appl. No. 13/835,735 Dated Oct. 13, 2015.
[NPL565] Office Action in U.S. Appl. No. 13/836,079 Dated Apr. 17, 2015.
[NPL566] Office Action in U.S. Appl. No. 13/836,079 Dated Jun. 30, 2016.
[NPL569] Office Action in U.S. Appl. No. 13/791,755 Dated Mar. 16, 2016.
[NPL570] Office Action in U.S. Appl. No. 13/791,755 Dated Aug. 9, 2016.
[NPL571] Office Action in U.S. Appl. No. 13/835,735 Dated Jun. 16, 2016.
[NPL572] Office Action in U.S. Appl. No. 13/836,079 Dated Nov. 6, 2015.
[NPL57] U.S. Appl. No. 13/424,467.
[NPL584] Office Action in App. No. AU 2015280604 mailed Apr. 8, 2016.
[NPL586] International Search Report from International Application No. PCT/US2014/014347 dated May 9, 2014.
[NPL590] PCT/US2016/030319 Written Opinion mailed Jul. 27, 2016.
[NPL591] PCT/US2016/030320 Written Opinion mailed Jul. 27, 2016.
[NPL596] PCT/US2012/014347, International Search Report.
[NPL5] PCT/US2015/016273 International Search Report and Written Opinion mailed Jun. 9, 2015.
[NPL601] Wester et al., A regenerable postassium and phosphate sorbent system to enhance dialysis efficacy and device portability: an in vitro study Nephrol Dial Transplant (2013) 28: 2364-2371 Jul. 3, 2013.
[NPL602] Office Action in App. No. JP 2016-515476 mailed Dec. 26, 2016.
[NPL603] Japanese Patent Publication No. S50-70281A.
[NPL605] PCT/US2015/032494 Written Opinion mailed Nov. 19, 2015.
[NPL606] PCT/US2015/032494 International Search Report mailed Nov. 19, 2015.
[NPL607] PCT/US2015/019901 International Preliminary Report on Patentability mailed May 27, 2016.
[NPL608] PCT/US2015/019901 Written Opinion mailed May 27, 2016.
[NPL609] PCT/US2015/019901 Written Opinion mailed Jun. 5, 2015.
[NPL610] PCT/US2015/019901 International Search Report mailed Jun. 5, 2015.
[NPL611] PCT/US2015/032485 International Preliminary Report on Patentability mailed May 11, 2016.
[NPL612] PCT/US2015/032485 International Preliminary Report on Patentability mailed May 11, 2016.
[NPL613] PCT/US20115/032485 International Preliminary Report on Patentability mailed May 11, 2016.
[NPL614] PCT/US2016/030304 International Search Report mailed Jul. 27, 2016.
[NPL615] PCT/US2016/030304 Written Opinion mailed Jul. 27, 2016.
[NPL616] PCT/US2016/030312 Written Opinion mailed Jul. 28, 2016.
[NPL617] PCT/US2016/030312 International Search Report mailed Jul. 28, 2016.
[NPL618] PCT/US2016/030319 International Search Report mailed Jul. 27, 2016.
[NPL619] PCT/US2016/030319 Written Opinion mailed Jul. 27, 2016.
[NPL620] PCT/US2016/030320 Written Opinion mailed Jul. 28, 2016.
[NPL621] PCT/US2016/030320 International Search Report mailed Jul. 28, 2016.

(56) References Cited

OTHER PUBLICATIONS

[NPL622] PCT/US2015/032485 Written Opinion mailed Oct. 16, 2015.
[NPL623] PCT/US2015/032485 Written Opinion mailed Oct. 16, 2016.
[NPL626] PCT/US2015/032485 International Search Report and Written Opinion mailed Oct. 16, 2015.
[NPL62] U.S. Appl. No. 13/424,533.
[NPL634] PCT/US2016/030320 International Preliminary Report on Patentability, mailed Apr. 20, 2017.
[NPL654] International Preliminary Report from International Application No. PCT/US2014/014348 dated Jan. 9, 2015.
[NPL655] European Search Report from European Application No. EP 14746193.3 dated Oct. 19, 2016.
[NPL656] European Search Report from European Application No. EP 14746193.3 dated Jun. 8, 2016.
[NPL657] PCT/US2014/014345 Written Opinion dated Jun. 24, 2015.
[NPL658] PCT/US2014/014345 International Search Report and Written Opinion dated May 30, 2014.
[NPL659] Office Action in European Application No. 14746428.03 dated Feb. 8, 2017.
[NPL660] European Search Report in European Application No. 14746428.03 dated Aug. 25, 2016.
[NPL661] PCT/US2014/014346 Writtent Opinion dated Apr. 10, 2015.
[NPL662] PCT/US2014/014346 International Search Report and Writtent Opinion dated May 23, 2014.
[NPL663] Ep 14746415.0 European Search Report dated Aug. 22, 2016.
[NPL664] Office Action in European Application No. EP 14746415.0 dated Apr. 19, 2017.
[NPL670] Office Action in European Application No. 14746415.0 dated Apr. 19, 2017.
[NPL67] U.S. Appl. No. 13/424,490.
[NPL681] PCT/US2015/020047 International Search Report and Written Opinion mailed Jun. 29, 2015.
[NPL682] PCT/US2015/020047 International Preliminary Report on Patentability mailed Jun. 30, 2015.
[NPL684] PCT/US2015/020044 Written Opinion dated Jun. 21, 2016.
[NPL685] PCT/US2015/020044 International Preliminary Report on Patentability dated Nov. 4, 2016.
[NPL686] PCT/US2015/020044 International Search Report dated Jun. 30, 2015.
[NPL688] US2015/019881 Written Opinion dated Jun. 16, 2016.
[NPL689] US2015/019881 Written Opinion dated May 9, 2016.
[NPL68] U.S. Appl. No. 13/424,517.
[NPL690] US2015/019881 International Search Report and Written Opinion dated Jun. 29, 2015.
[NPL692] PCT/US2014/065950 International Preliminary Report on Patentability mailed Oct. 28, 2015.
[NPL696] PCT/US2015/032485 Written Opinion mailed May 9, 2016.
[NPL6] PCT/US2015/032492 Written Opinion mailed Nov. 19, 2015.
[NPL720] PCT/US2015/019901 International Search Report and Written Opinion mailed Jun. 5, 2015.
[NPL721] PCT/US2015/019901 International Preliminary Report on Patentability mailed May 27, 2016.
[NPL722] PCT/US2015/032494 International Preliminary Report on Patentablity mailed Dec. 27, 2016.
[NPL730] Office Action for Chinese Application No. 201580009562.5 dated Jul. 3, 2017.
[NPL734] International Preliminary Report on Patentability for Application No. PCT/US2015/032492 dated Jun. 30, 2017.
[NPL736] Office Action in European Application No. 14746193.3 dated Apr. 19, 2017.
[NPL737] International Preliminary Report on Patentability for Application No. PCT/US2015/016273 dated Feb. 19, 2016.
[NPL747] European Search Report for App. No. 15751391.2 dated Aug. 4, 2017.
[NPL755] European Search Report and supplementary Search Report for App. No. 14865374.4 dated Jun. 12, 2017.
[NPL756] European Search Report and Supplemental Search Report in European Application No. 14865374.4 dated Jun. 12, 2017.
[NPL7] PCT/US2015/020046 International Search Report and Written Opinion mailed Jun. 29, 2015.
[NPL81] U.S. Appl. No. 61/480,539 dated Apr. 29, 2011.
[NPL84] U.S. Appl. No. 61/480,535 dated Apr. 29, 2011.
[NPL8] PCT/US2015/020044 International Search Report Written Opinion mailed Jun. 30, 2015.
[NPL90] Nedelkov, et. al., Design of buffer exchange surfaces and sensor chips for biosensor chip mass spectrometry, Proteomics, 2002, 441-446, 2(4).
[NPL] European Search Report App 14865374.4, Jun. 12, 2017.
Chinese Office Action in App. No. 201580009563.X, dated Mar. 13, 2018.
European Search Report for App. No. 15812081.6, dated Mar. 8, 2018.
European Search Report for App. No. 18153940.4, Dated Jun. 12, 2018.
European Search Report for App. No. 18153940.4, dated Sep. 28, 2018.
European Search Report for App. No. 19191469.6, dated Jan. 8, 2020.
European Search Report for EP 15811439, dated Feb. 15, 2018.
European Search Report for EP App. No. 15810804.3, dated Feb. 15, 2018.
European Search Report for EP App. No. 15811326.6, dated Feb. 14, 2018.
European Search Report for EP App. No. 15811573.3, dated Feb. 15, 2018.
European Search Report for EP App. No. 15812413.1, dated Feb. 2, 2018.
European Search Report for EP18177673.3-1104 (dated Oct. 19, 2018).
European Search Report for EP18177683.2-1104 (dated Nov. 8, 2018).
European Search Report in EP 15811454, dated Feb. 15, 2018.
European Search Report in EP 15812559.1, dated Jan. 31, 2018.
Office Action for Chinese App. No. 201711179516.7, dated Sep. 11, 2019.
Office Action for Chinese App. No. 201810042927, dated Sep. 23, 2019.
Office Action for European App. No. 17203968.7, dated Nov. 14, 2019.
Office Action in Japanese Application No. 2016-553344, dated Apr. 24, 2018.
PCT/US2016/030304_IPRP.
PCT/US2016/030319_IPRP.
Search Report for EP App. No. 17203984.4, dated Mar. 29, 2018.
Search Report for European App. No. 19187736.4, dated Dec. 16, 2019.
Search Report in EP App. No. 15752771, Dated Nov. 22, 2017.

* cited by examiner

PRECISION DIALYSIS THERAPY BASED ON SORBENT EFFLUENT ANALYSIS

CROSS-REFERENCE TO RELATED APPLICATION

This application claims the benefit of and priority to U.S. Provisional Patent Application No. 62/718,460 filed Aug. 14, 2018, the entire disclosure of which is incorporated by reference herein.

FIELD OF THE INVENTION

The invention relates to devices, systems, and methods for preforming a precision or personalized dialysis therapy session based on parameters obtained when introducing an ammonium removal solution through a zirconium phosphate sorbent module. The settings for the precision dialysis therapy session can be obtained by estimating a patient's physiological state such as blood urea nitrogen (BUN) level, based on an analysis of an effluent of the ammonium removal solution. The systems and methods include obtaining data while introducing the ammonium removal solution through zirconium phosphate in a sorbent module and determining a total ammonia content or pH of the ammonium removal solution effluent to estimate the patient's pre-dialysis physiological state.

BACKGROUND

Known dialysis systems and methods of treatment typically deliver dialysis with a fixed set of parameters with little to no monitoring of a patient's physiological parameters and no adjustment of dialysis parameters based on the patient's physiological state. The known systems generally fail to adjust parameters such as dialysate flow rate, blood flow rate, dialyzer size, amount of zirconium phosphate, sorbent module size or capacity, a bicarbonate addition profile, or combinations thereof, based on a patient blood urea nitrogen (BUN) level. Known dialysis therapy generally uses a monthly blood analysis, which is then used to determine if adjustments are needed to improve clearance. Monthly analysis can be ineffective given the day to day or week to week variability in the patient's physiological state due to diet, disease state, or session variability. As such, known dialysis systems and methods are incapable of providing precision or personalized dialysis therapy or providing updated or adjusted therapy based on feedback obtained about a patient's physiological status.

Urea is an important marker for dialysis adequacy in hemodialysis treatment that can factor into setting dialysis parameters for a dialysis therapy session. To measure a patient's blood urea nitrogen (BUN) level, existing systems and methods usually require a technician to obtain a blood sample from the patient. The technician then uses a blood gas analyzer to analyze the blood sample to determine BUN. The known process for obtaining BUN is expensive and time-consuming and relies on many manual steps that are not easily automatable. As such, BUN is infrequently used to adjust dialysis parameters even though it is an important adequacy indicator.

Hence, there is a need for systems and methods for preforming a precision dialysis therapy session based on the physiological parameters of the patient, such as patient BUN level. The need includes adjusting parameters such as dialysate flow rate, blood flow rate, dialyzer size, zirconium phosphate sorbent module size, a sorbent cartridge size, a bicarbonate addition profile, session frequency and timing, or combinations thereof based on the observed patient physiological state in a manner closer to real-time. The need includes obtaining information about a patient's physiological state in a non-invasive form. The need includes analyzing an effluent of an ammonium removal solution introduced through a zirconium phosphate sorbent module to determine a patient's physiological state such as an amount of ammonia. The need extends to measuring pre-dialysis BUN i.e., pre-BUN levels, using measurements from fluids excluding a patient's blood. The need extends to automated systems and methods for estimating a patient's physiological states and adjusting dialysis therapy based on the analysis.

SUMMARY OF THE INVENTION

The first aspect of the invention relates to a method. In any embodiment the method can comprise the step of setting at least one dialysis parameter for a subsequent dialysis session for a patient based on at least one fluid parameter of an ammonium removal solution effluent; wherein the at least one fluid parameter of the ammonium removal solution effluent is determined in either an effluent line fluidly connected to a sorbent module containing zirconium phosphate, or a reservoir fluidly connected to the effluent line.

In any embodiment, the at least one fluid parameter can be received from a sensor in the effluent line or in the reservoir fluidly connected to the effluent line.

In any embodiment, the at least one fluid parameter can comprise a total ammonia content in the ammonium removal solution effluent of a sorbent module; and the total ammonia content in the ammonium removal solution effluent is received from an ammonia sensor.

In any embodiment, the method can comprise the step of estimating a patient pre-dialysis BUN level based on the total ammonia content of the ammonium removal solution effluent.

In any embodiment, the step of setting at least one dialysis parameter for the subsequent dialysis session can comprise setting at least one of: a dialysate flow rate, a blood flow rate, a dialyzer size, a zirconium phosphate sorbent module size, a sorbent cartridge size, minimum zirconium phosphate requirements for treatment, a bicarbonate addition profile, dialysis session timing, dialysis session time, dialysis session frequency, or combinations thereof.

In any embodiment, the step of setting at least one dialysis parameter for the subsequent dialysis session can comprise reducing a dialysate flow rate, reducing a blood flow rate, reducing a dialyzer size, reducing a zirconium phosphate sorbent module size, reducing a sorbent cartridge size, increasing, a bicarbonate addition profile, decreasing a dialysis session frequency, or combinations thereof in response to a patient pre-dialysis BUN level below a patient pre-dialysis BUN level for a prior dialysis session.

In any embodiment, the at least one sensor can comprise a pH sensor or a temperature sensor.

In any embodiment, the method can use a sorbent recharger, and the method can comprise the step of recharging zirconium phosphate in a sorbent module by introducing one or more recharge solutions through the sorbent module; wherein the one or more recharge solutions comprises at least water and a brine solution.

In any embodiment, the method can be performed by a processor of a sorbent recharger.

In any embodiment, the processor can be programmed to receive an ammonia content of the ammonium removal solution effluent at preset intervals or continuously.

The features disclosed as being part of the first aspect of the invention can be in the first aspect of the invention, either alone or in combination, or follow a preferred arrangement of one or more of the described elements.

The second aspect of the invention is drawn to a system. In any embodiment, the system can comprise an ammonium removal flow path comprising: at least one ammonium removal solution source; the ammonium removal solution source fluidly connectable to a zirconium phosphate module inlet; a pump; and an effluent line fluidly connectable to a zirconium phosphate module outlet; either the effluent line comprising at least one sensor or further comprising a reservoir fluidly connected to the effluent line, the reservoir comprising at least one sensor; and a processor in communication with the at least one sensor, the processor setting at least one dialysis parameter for a subsequent dialysis session of a patient based on the at least one sensor.

In any embodiment, the at least one sensor can be positioned in the effluent line.

In any embodiment, the at least one sensor can be positioned in the reservoir fluidly connected to the effluent line.

In any embodiment, wherein the at least one sensor can be an ammonia sensor.

In any embodiment, the at least one sensor can further comprise a pH sensor or a temperature sensor.

In any embodiment, wherein the at least one sensor can be a conductivity sensor.

In any embodiment, the at least one dialysis parameter can be selected from: a dialysate flow rate, a blood flow rate, a dialyzer size, a zirconium phosphate sorbent module size, a sorbent cartridge size, a bicarbonate addition profile, dialysis session timing, dialysis session time, dialysis session frequency, or combinations thereof.

In any embodiment, the at least one dialysis parameter can be a bicarbonate addition profile.

In any embodiment, the system can comprise a sorbent recharger, and the ammonium removal flow path can be a zirconium phosphate recharging flow path fluidly connected to at least one recharge solution source, wherein at least one recharge solution source comprises at least a water source and a brine source.

In any embodiment, the processor can further estimate a patient pre-dialysis BUN level.

In any embodiment, the processor can be programmed to receive a fluid parameter from the at least one sensor at preset intervals or continuously.

The features disclosed as being part of the second aspect of the invention can be in the second aspect of the invention, either alone or in combination, or follow a preferred arrangement of one or more of the described elements.

DETAILED DESCRIPTION OF THE INVENTION

Figure 1:
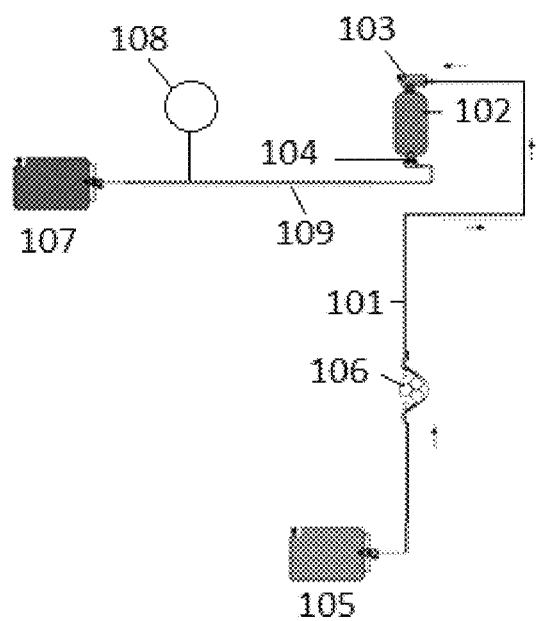
FIG. 1 is an ammonium removal flow path for removing ammonium ions from zirconium phosphate in a sorbent module.

Unless defined otherwise, all technical and scientific terms used have the same meaning as commonly understood by one of ordinary skill in the art.

The articles "a" and "an" are used to refer to one or to over one (i.e., to at least one) of the grammatical object of the article. For example, "an element" means one element or over one element.

An "ammonia sensor" can be any component or set of components capable of determining a concentration of ammonia within a fluid. In certain embodiments an ammonia sensor can determine ammonia, or ammonium, or both ammonia and ammonium ion concentration in a fluid.

"Ammonia" can refer to any amount of ammonia and/or ammonium in solution.

The term can also refer to an amount of total ammonia in a solution or total amount of ammonia plus ammonium in solution.

An "ammonium removal flow path" can be a path through which fluid can travel while removing ammonium ions from a material. One non-limiting material can be a sorbent material.

An "ammonium removal solution" is any solution containing solutes that promote the release of ammonium ions from a material. One non-limiting material can be a sorbent material.

The term "ammonium removal solution source" refers to a source of a solution containing solutes that promote release of ammonium ions from a material, such as a sorbent material. In certain embodiments, the ammonium removal solution source can be an acid, base, sodium ions, potassium ions, calcium ions, magnesium ions, or combinations thereof.

The term "amount of zirconium phosphate minimally required for therapy" can refer to the lowest amount of zirconium phosphate that can be used in a dialysis session without ammonia breakthrough occurring.

A "bicarbonate addition profile" is a rate of addition of bicarbonate to dialysate during dialysis treatment. The bicarbonate addition profile can refer to a function that varies with time and/or volumetric flow, or alternatively to a constant rate of bicarbonate addition. The bicarbonate addition profile can include any one or more of plural rates, start/stop instructions, and length of time. The profile bicarbonate addition can also refer to a constant or variable rate specific to a particular patient or subject over time and/or volumetric flow. The bicarbonate addition profile can further include functions such as a curve or a line, or a set period of time "Blood flow rate" refers to an amount of blood pumped through an extracorporeal circuit in a given period of time.

A "brine solution" can be a solution containing salts and/or buffers containing solutes used in recharging a sorbent material. In certain embodiments, the brine solution can be a solution of a sodium salt, acetic acid, sodium acetate, or combinations thereof.

The term "brine source" refers to a source of a solution of salts and/or buffers containing solutes used in recharging a sorbent material. In certain embodiments, the brine source can contain a sodium salt, acetic acid, sodium acetate, or combinations thereof.

The terms "contain," "to contain," and "containing" when used in reference to a material refers to retaining that material as contents of a compartment, module, device, or structure.

The terms "communication" or "electronic communication" can refer to the ability to transmit electronic data, instructions, information wirelessly, via electrical connection, or any other electrical transmission between two components or systems.

The term "comprising" includes, but is not limited to, whatever follows the word "comprising." Use of the term indicates the listed elements are required or mandatory but that other elements are optional and may be present.

The term "consisting of" includes and is limited to whatever follows the phrase "consisting of" The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The term "continuously," when referring to a frequency of measurements, can refer to taking measurements without stopping during a process.

The terms "control," "controlling," or "controls" refer to the ability of one component to direct the actions of a second or one or more components.

The terms "determining" and "determine" can refer to ascertaining or identifying a particular state or desired state. For example, a system or fluid, or any measured variable(s) or feature(s) of a system or a fluid can be determined by obtaining sensor data, retrieving data, performing a calculation, or by any other known method.

"Dialysate flow rate" refers to an amount of dialysate pumped through a dialysate flow path in a given period of time.

A "dialysis parameter" can be any factor or variable indicative of a dialysis session that can affect the performance of dialysis therapy and/or the health of a patient during and after dialysis therapy.

A "dialysis session" can be any time period of any length during which a patient is treated by or undergoes dialysis, hemodialysis, hemofiltration, ultrafiltration, or other fluid removal therapy.

The term "dialysis session frequency" refers to a number of dialysis sessions a patient undergoes in a given period of time.

"Dialysis session time" refers to the length of a dialysis session.

"Dialysis session timing" refers to a length of time between dialysis sessions.

The term "dialyzer clearance" refers to a rate at which solutes pass through a dialyzer membrane.

The term "dialyzer size" refers to a surface area of a dialyzer membrane in a dialyzer.

The term "effluent" can refer to liquid, gas, or a combination thereof exiting a container, compartment, or cartridge.

An "effluent line" can be a fluid passageway, tube, or path of any kind into which liquid, gas, or a combination thereof exiting a container, module, or component can flow.

"Estimated," "estimating," to "estimate," or "estimation" can each refer to a determination of one or more parameters indirectly using one or more variables.

The term "fluidly connectable" refers to a capability for providing for the passage of fluid, gas, or combination thereof, from one point to another point. The capability of providing such passage can be any connection, fastening, or forming between two points to permit the flow of fluid, gas, or combinations thereof. The two points can be within or between any one or more of compartments of any type, modules, systems, components, such as rechargers, as described herein.

The term "fluidly connected" refers to a particular state such that the passage of fluid, gas, or combination thereof, is provided from one point to another point. The connection state can also include an unconnected state, such that the two points are disconnected from each other to discontinue flow. It will be further understood that the two "fluidly connectable" points, as defined above, can from a "fluidly connected" state. The two points can be within or between any one or more of compartments, modules, systems, components, and rechargers, all of any type.

A "fluid parameter" is any characteristic, feature, or measurable factor of a liquid, gas, or combination thereof.

The term "integrating" or to "integrate" refers to determining a total area under a curve for a particular function.

The terms "introducing," "introduced," or to "introduce" refers to directionally moving or flowing a fluid, a gas, or a combination thereof by any means known to those of skill in the art.

The term "length of time of a dialysis session" refers to the total amount of time from the beginning to end of a single dialysis session.

The term "necessary to stabilize the pH," when referring to a volume of a recharge solution, is the amount of the recharge solution that is introduced or pumped through a sorbent module before the pH of the effluent recharge solution approaches a constant or near-constant value.

A "patient" or "subject" can be a member of any animal species, preferably a mammalian species, optionally a human. The subject can be an apparently healthy individual, an individual suffering from a disease, or an individual being treated for a disease. In certain embodiments, the patient can be a human, sheep, goat, dog, cat, mouse or any other animal.

The term "patient pre-dialysis blood urea nitrogen (BUN) level" can refer to the amount of urea within the body of a patient prior to a dialysis session. The BUN measurement is generally given in units of mg/dl.

"Patient water volume" refers to the total amount of water in a patient.

The term "pH sensor" refers to a device for measuring the pH or hydrogen ion concentration of a fluid.

The term "positioned" refers to a component connected to or in contact with the feature being referred to. The contact can be fluid or electrical and is intended to be used in the broadest reasonable interpretation.

"Precision dialysis" refers to dialysis treatment wherein dialysis parameters are customized or personalized to be specifically applied or used by a particular patient, group, or class of patients. Precision dialysis is not limited to any particular standard but rather dependent upon input variables to achieve a desired dialysis state. Precision dialysis is an approach that can take into account individual variability and can include one or more parameters. In general, precision dialysis can provide for more accurate, effective, and/or economical dialysis. The approach is contrasted to a onesize-fits-all approach, in which dialysis relies on averages without any consideration of specific conditions, features, and factors, or any other variable that might have an impact on a specific dialysis.

A "preset interval" or "present intervals" can be a period of time between events that is determined prior to the events.

A "prior dialysis session" is a dialysis session that has already occurred.

The term "processor" as used is a broad term and is to be given its ordinary and customary meaning to a person of ordinary skill in the art. The term refers without limitation to a computer system, state machine, processor, or the like designed to perform arithmetic or logic operations using logic circuitry that responds to and processes the basic instructions that drive a computer. In any embodiment of the first, second, third, and fourth invention, the terms can include ROM ("read-only memory") and/or RAM ("random-access memory") associated therewith.

The term "programmed," when referring to a processor, can mean a series of instructions that cause a processor to perform certain steps.

The term "pump" refers to any device that causes the movement of fluids or gases by applying suction or pressure.

The terms "receiving," "to receive," or "received" refer to obtaining information or data from any source by any means including direct electrical contact, wireless transmission, and networked connection.

A "recharge solution" or "recharge solutions" can be a solution containing appropriate ions for recharging a specific sorbent material. A recharge solution can be a single solution containing all necessary ions for recharging a sorbent material. Alternatively, the recharge solution can contain some of the ions for recharging the sorbent material, and one or more other recharge solutions can be used to form a composite "recharge solution" to recharge the sorbent material, as described herein.

A "recharge solution source" can be any fluid or concentrate source from which a recharge solution can be stored, obtained, or delivered therefrom.

"Recharging" refers to treating a sorbent material to restore a functional capacity of the sorbent material putting the sorbent material back into a condition for reuse or use in a new dialysis session. In some instances, the total mass, weight and/or amount of "rechargeable" sorbent materials remain the same. In some instances, the total mass, weight and/or amount of "rechargeable" sorbent materials change. Without being limited to any one theory of invention, the recharging process may involve exchanging ions bound to the sorbent material with different ions, which in some instances may increase or decrease the total mass of the system. However, the total amount of the sorbent material will in some instances be unchanged by the recharging process. Upon a sorbent material undergoing "recharging," the sorbent material can then be said to be "recharged."

The term "reducing" or to "reduce" refer to setting one or more parameters to a lower quantity as compared to a prior setting.

A "reservoir" is a container or component that can hold a liquid, fluid, gas, or combination thereof.

The term "sensor," as used herein, can be a converter of any type that can measure a physical property or quantity of a matter in a solution, liquid or gas, and can convert the measurement into a signal which can be read by an electronic instrument.

The term "setting" or to "set" refers to the process of adjusting or controlling a variable to a desired value for use in a process or system.

A "sorbent cartridge module" or "sorbent module" means a discreet component of a sorbent cartridge. Multiple sorbent cartridge modules can be fitted together to form a sorbent cartridge of two, three, or more sorbent cartridge modules. The "sorbent cartridge module" or "sorbent module" can contain any selected materials for use in sorbent dialysis and may or may not contain a "sorbent material" or adsorbent, but less than the full complement of sorbent materials needed. In other words, the "sorbent cartridge module" or "sorbent module" generally refers to the use of the "sorbent cartridge module" or "sorbent module" in sorbent-based dialysis, e.g., REDY (REcirculating DYalysis), and not that a "sorbent material" that is necessarily contained in the "sorbent cartridge module" or "sorbent module."

The term "sorbent cartridge size" can refer to the amount of one or more sorbent materials within a sorbent module. The sorbent cartridge size can refer to a mass, volume, or functional capacity of the one or more sorbent materials.

A "sorbent recharger" or "recharger" is an apparatus designed to recharge at least one sorbent material.

A "subsequent dialysis session" is a dialysis session that will happen at a future time.

The term "temperature sensor" refers to a device for measuring the temperature of a gas, a liquid, or a combination thereof in a vessel, container, or fluid line.

The term "total ammonia content" can refer to an amount of ammonia dissolved in a fluid. The total ammonia content can refer to the concentration, mass, or any other value of the amount of ammonia dissolved in the fluid. In certain embodiments, the term ammonia content can refer to the sum of the ammonia content and/or ammonium ion content of a fluid.

"Urea reduction ratio" or "URR" refers to the amount by which the urea level of a patient is reduced during treatment. The URR can be expressed as 1 minus the ratio of the patient's ending urea level over the patient's starting urea level.

The term "volume averaged total ammonia content" can refer to a total ammonia content of a fluid divided by a total volume of the fluid.

A "water source" can be a fluid source from which water can be stored, obtained, or delivered therefrom.

"Zirconium phosphate" is a sorbent material that removes cations from a fluid, exchanging the removed cations for different cations.

The term "zirconium phosphate module inlet" can refer to a portion of a sorbent module containing zirconium phosphate through which fluid, gas, or a combination thereof can be drawn into the sorbent module.

The term "zirconium phosphate module outlet" can refer to a portion of a sorbent module containing zirconium phosphate through which fluid, gas, or a combination thereof can be drawn out of the sorbent module.

A "zirconium phosphate recharging flow path" can be a path through which fluid can travel while recharging zirconium phosphate in a sorbent module.

The term "zirconium phosphate sorbent module size" can refer to the amount of zirconium phosphate within a sorbent module. The zirconium phosphate sorbent module size can refer to a mass, volume, or functional capacity of the zirconium phosphate.

Zirconium Phosphate Ammonium Removal

The invention is drawn to systems and methods that can provide for adjustment of dialysis parameters based on data obtained about a patient's physiological status. The systems and methods can set one or more dialysis parameters based on analysis of a sorbent module effluent during removal of ammonium ions from a sorbent module containing zirconium phosphate used by the patient during a previous dialysis session. The settings can deliver precise or personalized dialysis to the patient based on the analysis of the effluent. The precision or personalized care can be performed by providing feedback using an analysis of a sorbent cartridge during removal of ammonium ions of a sorbent cartridge used by a particular patient. For example, an ammonium removal solution effluent from a sorbent cartridge linked to a particular patient can be used to estimate a patient's blood urea nitrogen level. The obtained information can then be used to adjust a future dialysis therapy session for that same patient. The settings for the precision dialysis therapy session can be obtained by estimating a patient blood urea nitrogen (BUN) level based on an analysis of the effluent during removal of ammonium ions for a particular sorbent module linked to a particular patient.

The systems and methods can be used to determine an amount of ammonium ions absorbed by the zirconium phosphate in a sorbent dialysis system. Zirconium phosphate is used to remove waste and unwanted solutes including ammonium, potassium, calcium, and magnesium ions from dialysate. The zirconium phosphate is commonly contained inside a sorbent cartridge. Zirconium oxide is used to remove phosphate ions from dialysate. Urease is used to breakdown urea into carbon dioxide and ammonium in order to facilitate their removal. During treatment, the ammonium ions are adsorbed by the zirconium phosphate to avoid being returned to the patient. The systems and methods can measure the amount of ammonium ions displaced from zirconium phosphate during an exchange process. The systems can take measurements and provide automated recommendations for setting a future dialysis therapy session for the patient.

FIG. 1 illustrates a non-limiting embodiment of the system. The system can include an ammonium removal flow path 101 fluidly connectable to an ammonium removal solution source 105. The ammonium removal solution source 105 can contain a solution of one or more solutes that will displace ammonium ions bound to zirconium phosphate in a zirconium phosphate sorbent module 102 during treatment. During a dialysis session, the zirconium phosphate serves to remove cations from spent dialysate, including ammonium, potassium, calcium, and magnesium, exchanging the cations for hydrogen and sodium ions. The ammonia is formed by the breakdown of urea by urease in the sorbent cartridge during treatment. The amount of ammonia adsorbed by the zirconium phosphate is therefore a function of the amount of urea removed during treatment. The ammonium removal solution in ammonium removal solution source 105 can contain any solutes that will displace the ammonium ions from the zirconium phosphate. In certain embodiments, the ammonium removal solution can contain sodium ions, calcium ions, magnesium ions, potassium ions, acid, or base. Because calcium and magnesium bind more strongly to the zirconium phosphate, an ammonium removal solution containing calcium or magnesium may be used when the zirconium phosphate sorbent module 102 is single use.

The zirconium phosphate sorbent module 102 can be fluidly connectable to the ammonium removal flow path 101 through zirconium phosphate module inlet 103 and zirconium phosphate module outlet 104. In certain embodiments, the zirconium phosphate sorbent module 102 can be reusable. Alternatively, the zirconium phosphate sorbent module 102 can be single-use. Pump 106 provides a driving force for moving fluids through the flow path. Ammonium ions displaced when solutes from the ammonium removal solution are adsorbed by the zirconium phosphate exit the zirconium phosphate sorbent module 102 through zirconium phosphate module outlet 104 into effluent line 109. In certain embodiments, an ammonia sensor 108 positioned in effluent line 109 can measure the total ammonia concentration of the ammonium removal solution effluent in effluent line 109. As described, a processor in communication with the ammonia sensor 108 can use the total ammonia content of the ammonium removal solution effluent to estimate the patient pre-dialysis BUN level. Alternatively, or additionally, the ammonium removal solution effluent can be collected in an effluent reservoir 107. The ammonium removal solution effluent collected in effluent reservoir 107 can be pooled and tested to measure the total ammonia content of the ammonium removal solution effluent. The pooled ammonium removal effluent can be tested with a sensor in the effluent reservoir 107, or tested with a test strip or other portable or disposable testing methods.

Although shown as a single ammonia sensor 108 in FIG. 1, the ammonia sensor 108 can alternatively be multiple sensors that determine individual parameters of the ammonium removal solution effluent to allow for calculation of the total ammonia content in the ammonium removal solution effluent. For example, the ammonia sensor 108 can be a combination of pH and ammonia sensors, a combination of pH and ammonium ion sensors, a combination of ammonia and ammonium ion sensors, or any one or more sensors that allow for calculation of the total ammonia content of the ammonium removal solution effluent. The ammonia sensor 108 can detect the total ammonia concentration in the ammonium removal solution effluent by any means. For example, one or more ammonia sensing membranes can be contacted with the ammonium removal solution effluent, the ammonia sensing membranes changing color or any other optical parameter in response to the total ammonia content in the ammonium removal solution effluent. The optical change in the ammonia sensing membrane can be detected by a photodetector to determine the ammonia content, ammonium content, pH, or combinations thereof. Any number of sensing membranes for determining the ammonia content, ammonium content, or pH can be included in the ammonia sensor 108. In certain embodiments, the ammonia sensor 108 can measure the partial pressure of ammonia gas in the ammonium removal solution effluent and then use Henry's law and the Henderson-Hasselbach equation to determine the total ammonia content. Alternatively, the ammonia sensor 108 can be an ion selective electrode measuring the ammonium ions in the ammonium removal solution effluent. Additional sensors, such as a temperature sensor (not shown) can be included to determine the total ammonia content of the ammonium removal solution effluent with methods that require the temperature to be known.

Figure 2:
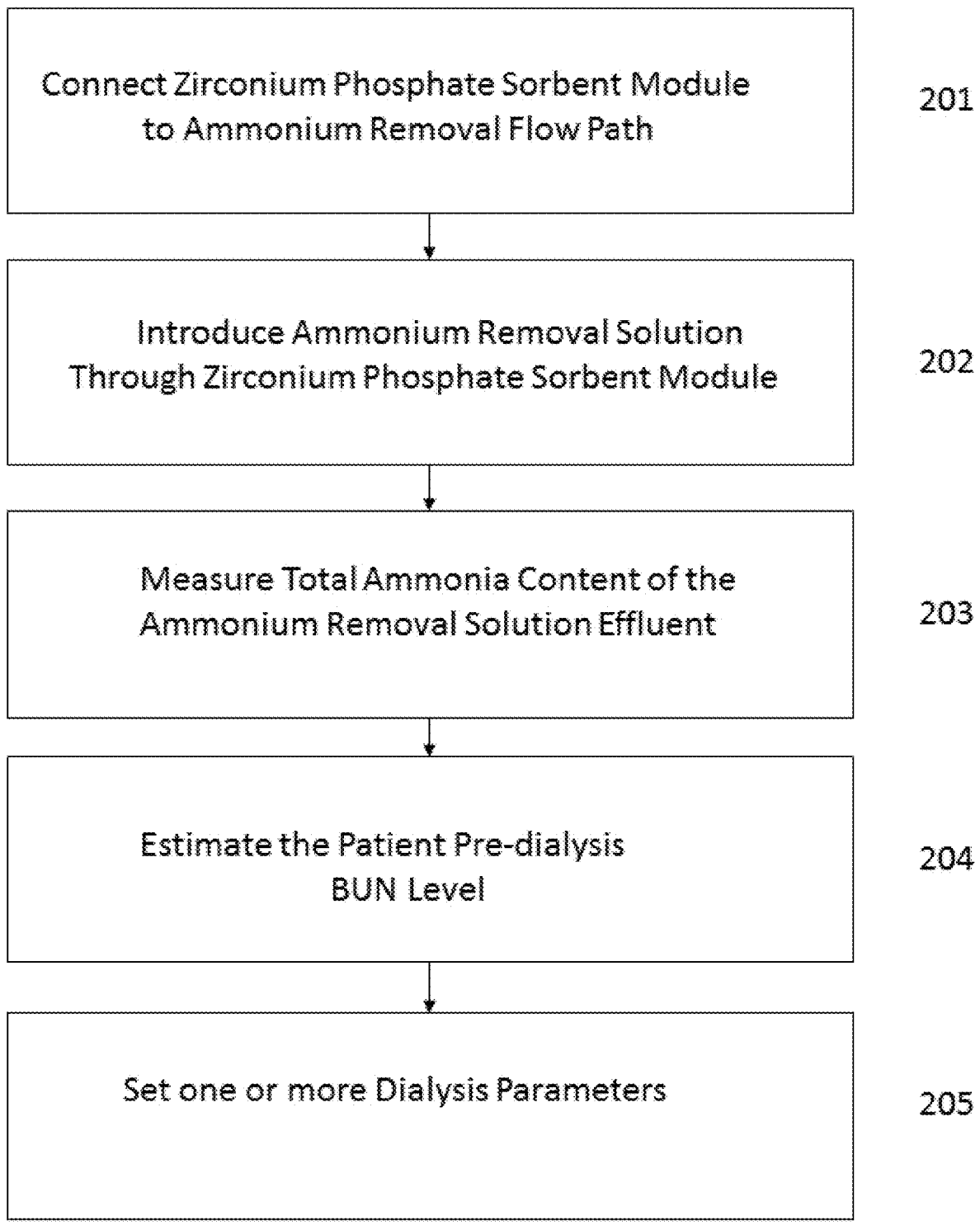
FIG. 2 is a flow chart illustrating a method for setting at least one dialysis parameter based on an estimate of a patient pre-dialysis BUN level.

FIG. 2 is a flow chart illustrating the method of estimating the patient pre-dialysis BUN level and adjusting one or more dialysis parameters based on the estimation. In step 201, a zirconium phosphate sorbent module that was used in a previous dialysis session can be placed into a system for removing ammonium ions by fluidly connecting an inlet and outlet of the zirconium phosphate sorbent module to a flow path as illustrated in FIG. 1. In step 202, an ammonium removal solution can be introduced through the zirconium phosphate sorbent module. As described, the ammonium removal solution can contain an acid, a base, sodium ions, potassium ions, calcium ions, magnesium ions, or any other ions that can displace the ammonium ions bound to the zirconium phosphate. In step 203, the processor can receive the total ammonia content in the ammonium removal solution effluent from an ammonia sensor either continuously or at preset intervals. In certain embodiments, the processor can receive the total ammonia content in the ammonium removal solution effluent at preset intervals of between 1 second and 5 minutes, including between 1 second and 30 seconds, between 1 second and 1 minute, between 30 seconds and 2 minutes, between 1 minute and 3 minutes, or between 2 minutes and 5 minutes. In certain embodiments, the processor can receive the total ammonia content of the ammonium removal solution effluent a single time and compare the total ammonium content of the ammonium removal solution effluent with known or characterized discharge/capacity curves using a lookup table or other method of comparison. The flow rate of the ammonium removal solution introduced through the zirconium phosphate sorbent module can also be received by the processor. Using the flow rates and total ammonia contents in the ammonium removal solution effluent, the processor can determine the volume averaged total ammonia content of the effluent. The processor can then estimate the patient pre-dialysis BUN level using the EQ's(1-9) provided herein, as described based on an analysis of the effluent received from the ammonia sensor in step 204. Alternatively, the ammonium removal solution effluent can be collected in a reservoir, and the total ammonia content measured in the reservoir. The total ammonia ions removed can be determined by multiplying the total ammonia content of the collected ammonium removal solution effluent by the total volume of ammonium removal solution used. In step 205, the processor can set one or more dialysis parameters for a subsequent dialysis session of the patient based on the patient pre-dialysis BUN level. Table 1 illustrates non-limiting dialysis parameters that can be set based on the patient pre-dialysis BUN level.

TABLE 1

| Dialysis Parameter | Change |
| --- | --- |
| Dialysate Flow Rate | Reduce Rate in Response to Lower BUN |
| Blood Flow Rate | Reduce Rate in Response to Lower BUN |
| Dialyzer Size | Reduce Size in Response to Lower BUN |
| Zirconium Phosphate Sorbent Module Size | Reduce Size in Response to Lower BUN |
| Sorbent Cartridge Size | Reduce Size in Response to Lower BUN |
| Amount of Zirconium Phosphate Minimally Required for Therapy | Reduce Amounts in Response to Lower BUN |
| Bicarbonate Addition Profile | Increase Addition Rate in Response to Lower BUN |
| Dialysis Session Timing | Increase Length of Time Between Sessions in Response to Lower BUN |
| Dialysis Session Time | Reduce Dialysis Session Time in Response to Lower BUN |
| Dialysis Session Frequency | Reduce Frequency in Response to Lower BUN |

A lower patient pre-dialysis BUN level can allow effective dialysis treatment with a reduced blood flow rate, dialyzer flow rate, and/or dialyzer size, as compared to a prior dialysis session for the patient because the patient has less urea that needs to be removed. Conversely, if the patient pre-dialysis BUN level is increasing, an increased blood flow rate, dialyzer flow rate, and/or dialyzer size can be used as compared to the prior dialysis session to compensate for the increased urea in the patient. A lower patient pre-dialysis BUN level also means that fewer ammonium ions will be adsorbed by the zirconium phosphate, and as a result, a smaller zirconium phosphate sorbent module can be used. Similarly, the amount of zirconium phosphate minimally required for therapy is lower for patients with lower pre-dialysis BUN levels because fewer ammonium ions will be adsorbed by the zirconium phosphate. A smaller sorbent cartridge can also be used if the patient BUN level is lower. A lower BUN level means the patient will have reduced clearance requirements, allowing treatment with a smaller sorbent cartridge, even if the patient weight wouldn't normally support the smaller size. A lower patient pre-dialysis BUN level also results in a lower amount of carbon dioxide produced by the breakdown of urea in the sorbent cartridge. Because the carbon dioxide is in equilibrium with bicarbonate in the spent dialysate, less carbon dioxide produced by the sorbent cartridge will result in less bicarbonate in the dialysate. As a result, the rate of addition of bicarbonate to the dialysate during treatment can be increased compared to a patient with a higher pre-dialysis BUN level. A lower patient pre-dialysis BUN level can also allow for adjustments to dialysis session timing dialysis session frequency, and dialysis session time. A patient with a lower patient pre-dialysis BUN level may be able to undergo dialysis less frequently, during a shorter time period per session, or with longer periods of time between dialysis sessions.

Zirconium Phosphate Recharging

Figure 3:
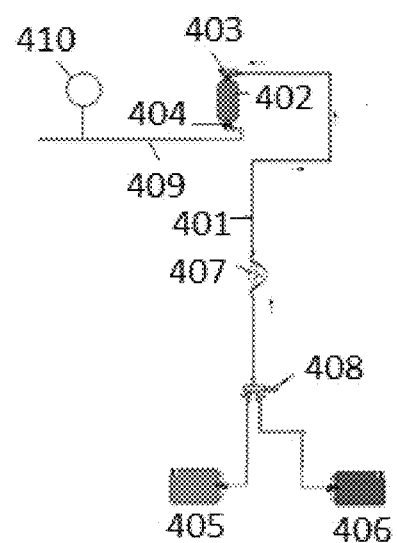
FIG. 3 is a recharging flow path for recharging zirconium phosphate in a sorbent module.

The amount of ammonium ions adsorbed by the zirconium phosphate can also be determined while recharging the zirconium phosphate in a zirconium phosphate sorbent module. Recharging a sorbent module containing zirconium phosphate can be performed as in U.S. patent application Ser. No. 14/642,847 (US20150367055A1), the contents of which are incorporated herein in their entirety. FIG. 3 illustrates a non-limiting embodiment of a zirconium phosphate recharging flow path 401 for recharging zirconium phosphate in a zirconium phosphate sorbent module 402. The recharging flow path 401 illustrated in FIG. 3 can also serve as an ammonium removal flow path for removing ammonium ions from the zirconium phosphate sorbent module 402. In certain embodiments, the zirconium phosphate sorbent module 402 can be a reusable sorbent module. After dialysis, the zirconium phosphate sorbent module 402 can be removed from the dialysis system and placed in the recharger. Alternatively, the zirconium phosphate sorbent module 402 can be a single-use or disposable sorbent module. The zirconium phosphate can be removed from the sorbent module and used in dialysis and placed in a new sorbent module for recharging. The zirconium phosphate sorbent module 402 can be fluidly connectable to the zirconium phosphate recharging flow path 401 through zirconium phosphate module inlet 403 and zirconium phosphate module outlet 404. Pump 407 provides a driving force for moving fluids through the zirconium phosphate recharging flow path 401. The zirconium phosphate recharging flow path 401 can include one or more recharge solution sources, including a brine source 405 and a water source 406. The brine source 405 can contain a brine solution of a salt, such as sodium chloride, and a buffer, such as a mixture of sodium acetate and acetic acid. The recharge solutions act as the ammonium removal solution, with the sodium and hydrogen ions in the recharge solution displacing the ammonium ions adsorbed by the zirconium phosphate during a prior dialysis session. Although shown as a single brine source 405, multiple recharge solution sources can be used. For example, a first recharge solution source containing sodium chloride and a second recharge solution source containing an acetate buffer. Alternatively, three recharge solution sources can be used, with sodium chloride, sodium acetate, and acetic acid in separate recharge solution sources. If multiple recharge solution sources are used, the recharge solutions can be mixed within the zirconium phosphate recharging flow path 401 or pumped through the zirconium phosphate sorbent module 402 sequentially. Any combination of sodium salt and buffer capable of causing exchange of ammonium, potassium, calcium, and magnesium for sodium and hydrogen ions can be used as the recharge solutions. Optional valve 408 can be included to control the movement of fluid from either the brine source 405 or water source 406. Alternatively, separate pumps on fluid lines fluidly connected to each recharge solution source can be used. A processor (not shown) can be programmed to control the pumps or valves to direct recharge solutions from the recharge solution sources through the zirconium phosphate sorbent module 402. One of skill in the art will understand that multiple pump and valve arrangements can be used to pump the necessary recharge solutions through the zirconium phosphate sorbent module 402.

A sensor 410 positioned in the effluent line 409 can determine at least one fluid parameter of the effluent recharge solution in effluent line 409. In certain embodiments, the sensor 410 can be an ammonia sensor, a pH sensor, or a combination thereof. In certain embodiments, conductivity sensors can be used to measure the total ammonia content of the ammonium removal solution effluent. As described, an ammonia sensor in effluent line 409 can be used to estimate the patient pre-dialysis BUN level.

During a dialysis session, the zirconium phosphate serves to remove cations from spent dialysate, including ammonium, potassium, calcium, and magnesium, exchanging the cations for hydrogen and sodium ions. The sodium chloride and buffer solutions used in recharging the zirconium phosphate serve to displace the cations absorbed during treatment with sodium and hydrogen ions, facilitating reuse of the zirconium phosphate.

The ammonia is formed by the breakdown of urea by urease in the sorbent cartridge during treatment. The amount of ammonia adsorbed by the zirconium phosphate is therefore a function of the amount of urea removed during treatment. Displaced ammonia from the zirconium phosphate sorbent module 402 will exit the zirconium phosphate sorbent module 402 through zirconium phosphate module outlet 404 into effluent line 409. An ammonia sensor in the effluent line 409 can determine the total ammonia content of the effluent recharge solution, which is similar to the ammonium removal solution effluent described in FIGS. 1-2. One of skill in the art will understand that several methods can be used to determine the total ammonia content in the effluent line 409. In certain embodiments, the sensor 410 can determine concentrations of both ammonia and ammonium ions in the effluent line 409. Alternatively, the ammonia sensor can determine either the ammonia or ammonium ion concentration and the pH, allowing the total ammonia content to be determined using the Henderson-Hasselbach equation. In certain embodiments, the ammonia sensor can measure the partial pressure of ammonia gas, with the total ammonia content of the effluent determined using Henry's law and the Henderson-Hasselbach equation. Additional sensors, such as a temperature sensor can also be used. Although a single sensor 410 is illustrated in FIG. 3, the ammonia sensor can alternatively be multiple sensors that determine individual parameters of the effluent recharge solution to allow for calculation of the total ammonia content in the effluent recharge solution. The ammonia sensor can be in communication with a processor (not shown) programmed to estimate the patient pre-dialysis BUN level based on an analysis of the effluent received from the ammonia sensor, and the processor can use the patient pre-dialysis BUN level to set one or more dialysis parameters for a patient. In certain embodiments, an effluent reservoir (not shown) can be fluidly connectable to effluent line 409. The total ammonia content of the collected effluent can be measured to determine the total amount of ammonium ions removed from the zirconium phosphate during recharging.

During the ammonium removal process, the ammonium removal solution can be introduced through the zirconium phosphate sorbent module 402 in either direction. The ammonium removal solution can be introduced through the zirconium phosphate sorbent module 402 in the same direction as the dialysate flow during therapy, or in the reverse direction. Generally, when recharging the zirconium phosphate sorbent module 402, the direction of flow of the recharge solutions is in the reverse direction as compared to the dialysate flow during treatment. However, when the ammonium removal solution is introduced in the same direction as the dialysate flow during therapy, the amount of time required before ammonia is detected in the effluent can provide an indication of the amount of ammonium ions removed by the zirconium phosphate sorbent module 402 during therapy. Generally, only the most proximal portion of the zirconium phosphate sorbent module 402 will be saturated with ammonium ions during therapy and the distance ammonium ions travel through the zirconium phosphate sorbent module 402 during therapy is a function of the amount of ammonium ions removed. The length of time during ammonium removal prior to detection of ammonia in the effluent is a function of the amount of ammonium ions removed during therapy.

Figure 4:
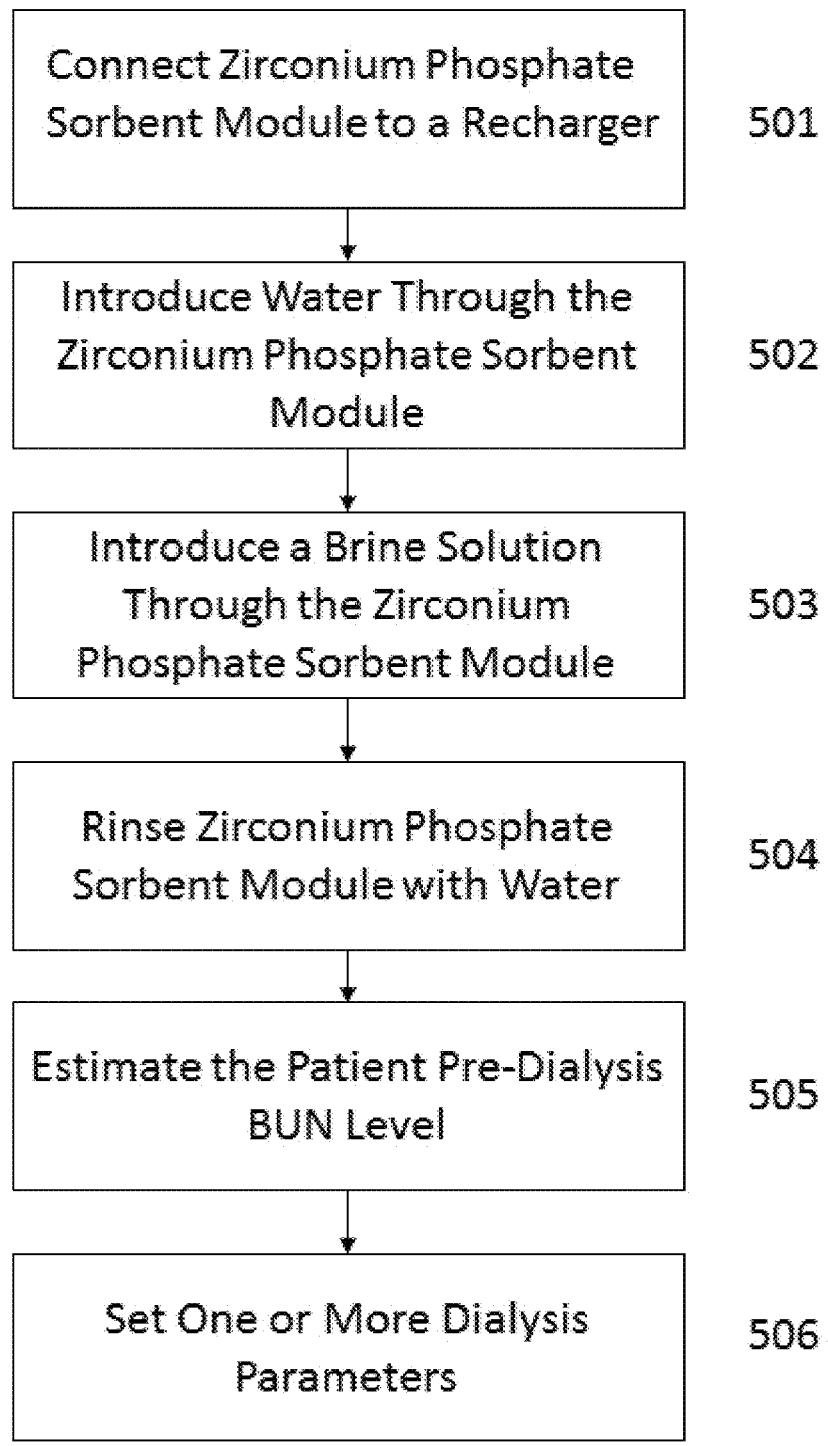
FIG. 4 is a flow chart illustrating a method for setting at least one dialysis parameter based on an estimate of a patient pre-dialysis BUN level obtained during recharging of zirconium phosphate in a sorbent module.
Figure 5:
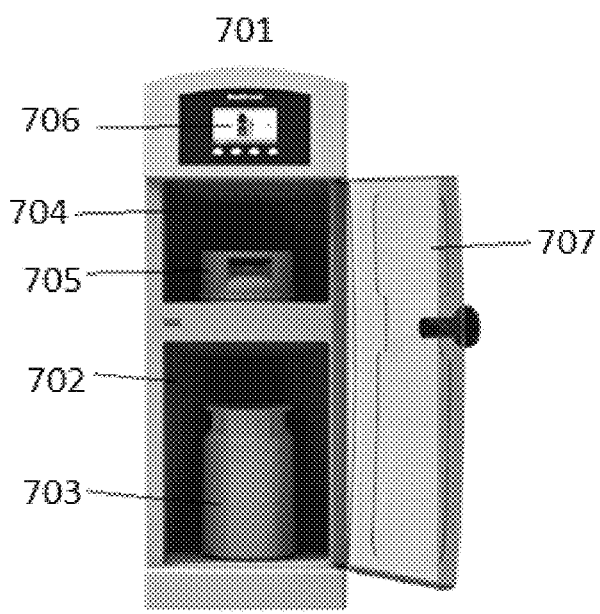
FIG. 5 is a non-limiting embodiment of a sorbent recharger.

FIG. 4 illustrates a flow chart for the method of estimating the patient pre-dialysis BUN level and setting one or more dialysis parameters for the patient in response to the patient pre-dialysis BUN level during recharging. In step 501, a zirconium phosphate sorbent module containing zirconium phosphate that was used in a previous dialysis session can be placed in a receiving compartment of a sorbent recharger and fluidly connected to a zirconium phosphate module inlet and a zirconium phosphate module outlet, as illustrated in FIG. 3. In step 502, water from a water source can be introduced or pumped through the zirconium phosphate sorbent module to rinse the zirconium phosphate sorbent module. In a preferred embodiment, the processor can begin receiving the total ammonia content in the effluent recharge solution during step 502. However, in certain embodiments, the determining the total ammonia content can begin after introducing, pumping, or flowing a brine solution through the zirconium phosphate sorbent module in step 503. As described, the brine solution can contain a sodium salt and a buffer. The brine solution can be introduced or pumped through the zirconium phosphate sorbent module in step 503 as a single solution, or alternatively any combination of sodium salt, acid, and base can be pumped through the zirconium phosphate sorbent module sequentially. In step 504, water can be again pumped or introduced through the zirconium phosphate sorbent module to remove the brine solution still remaining in the zirconium phosphate sorbent module. The processor can receive the total ammonia content in the effluent recharge solution from the ammonia sensor or the pH from a pH sensor either continuously, at preset intervals, or a single time. When a single total ammonia content determination is made the processor can compare the ammonium content of the effluent at the single point in time with known or characterized discharge/capacity curves using a lookup table or other method of comparison. When total ammonia determinations are made at preset intervals the processor can compare the ammonium content of the effluent at the intervals with known curves, providing a higher level of accuracy and confidence in the calculations. With continuous ammonia content determinations, or with determinations in smaller intervals, the processor can integrate the total ammonia content of the effluent to calculate the amount of ammonium ions removed from the zirconium phosphate, or compare the multiple total ammonia measurements with known curves and a high degree of confidence. In certain embodiments, the processor can receive the total ammonia content in the effluent recharge solution at preset intervals of between 1 second and 5 minutes, including between 1 second and 30 seconds, between 1 second and 1 minute, between 30 seconds and 2 minutes, between 1 minute and 3 minutes, or between 2 minutes and 5 minutes. The flow rate of the recharging solutions pumped through the zirconium phosphate sorbent module can also be received by the processor. Using the flow rates and total ammonia contents in the sorbent recharger effluent recharge solution, the processor can determine the volume averaged effluent recharge solution total ammonia content. The processor can then estimate the patient pre-dialysis BUN level using the EQ's(1-9), as described based on an analysis of the effluent received from the ammonia sensor in step 505. In step 506, the processor can set one or more dialysis parameters for a subsequent dialysis session of the patient based on the patient pre-dialysis BUN level, as described. FIG. 5 illustrates a non-limiting embodiment of a sorbent recharger 701 for recharging zirconium phosphate in a zirconium phosphate sorbent module 703. The sorbent recharger 701 can include a receiving compartment 702 for receiving a zirconium phosphate sorbent module 703. Fluid connections (not shown in FIG. 5) connect to the top and bottom of the zirconium phosphate sorbent module 703 for passing recharge solutions into, through and out of the zirconium phosphate sorbent module 703. As described, the recharging fluids replace ions bound to the sorbent materials during dialysis with new ions, recharging the zirconium phosphate within the zirconium phosphate sorbent module 703, allowing reuse of the zirconium phosphate sorbent module 703 in dialysis. The sorbent recharger 701 can also have an optional second receiving compartment 704 for receiving a second sorbent module 705, which is also fluidly connected to recharge solution sources for recharging of second sorbent module 705. In certain embodiments, the second sorbent module 705 can also contain zirconium phosphate, allowing multiple zirconium phosphate sorbent modules to be recharged concurrently. Alternatively, the second sorbent module 705 can contain a different sorbent material, such as zirconium oxide. A user interface 706 can be provided to start or control the recharging process by the user and to receive information from the sorbent recharger 701, such as the patient pre-dialysis BUN level. The user interface 706 can also provide the status of the recharging process to the user, such as the time to completion for each recharging step, or a time to complete the entire recharging process. User interface 706 provides alert messages if any problems are detected during recharging, such as leaks, occlusions, pump failures, or mismatched chemicals. A door 707 on the sorbent recharger 701 controls access to the receiving compartments 702 and 704 during operation.

The sorbent recharger 701 can have one or more processors for determining an ammonia level in the recharger effluent. The sorbent recharger 701 can transmit data obtained from a sensor wirelessly or by wired connection. The data needed to make a determination of the total ammonia content can be communicated to another component such as a dialysis machine that can then determine the total ammonia content, match the data to a particular patient, and adjust the specific parameters for performing a dialysis therapy session for that patient. The sorbent recharger 701 can be connected to a local area network (LAN) or a secure internet connection that transmits the required instructions or data to a component that either process the data or performs a set of instructions. It will be understood that the determination and calculation of total ammonia content in the recharger effluent is not limited to a component physically attached to the recharger or other component local to the dialysis system, but can be performed at any local or remote data center including cloud infrastructure, or other network of remote servers hosted on the Internet that can store, manage, and process data. The networked systems can be secured by any known methods and procedures as known to those of skill in the art.

Although illustrated in FIG. 5 as having two receiving compartments 702 and 704, a sorbent recharger for recharging a single sorbent material can have a single receiving compartment or multiple receiving compartments for receiving and recharging multiple modules containing the same sorbent material. Sorbent rechargers with any number of receiving compartments for recharging any number or combination of zirconium oxide and/or zirconium phosphate sorbent modules can be constructed. For example, a sorbent recharger with two zirconium phosphate receiving compartments and two zirconium oxide receiving compartments can be similarly constructed. The rechargers can have 1, 2, 3, 4, 5, 6, or more receiving compartments, each capable of receiving zirconium oxide or zirconium phosphate sorbent modules.

Figure 6:
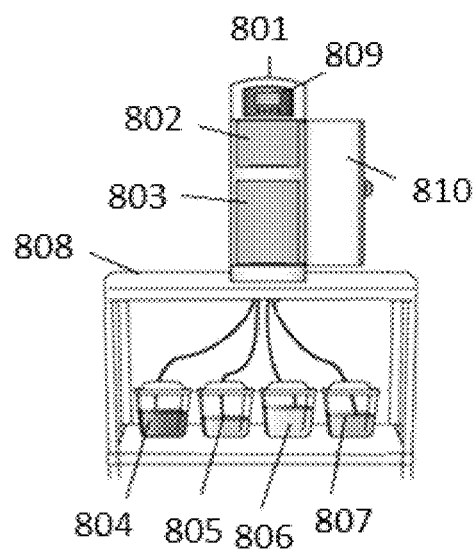
FIG. 6 is a sorbent recharger configured to recharge zirconium phosphate.

FIG. 6 illustrates a non-limiting embodiment of a sorbent recharger 801 set up for recharging zirconium phosphate. To recharge the zirconium phosphate, one or more recharging fluids can be passed through a zirconium phosphate sorbent module. As shown in FIG. 6, the sorbent recharger 801 can be fluidly connected to one or more recharging fluid sources, such as water source 804, sodium chloride source 805, buffer source 806, and disinfectant source 807. As described, the sodium chloride and buffer can be combined into a single brine source (not shown in FIG. 6). Alternatively, the buffer source 806 can be replaced by separate acid and base sources. Any number of recharge solution sources can be included. The sorbent recharger 801 has a zirconium phosphate receiving compartment 802. Optionally, the sorbent recharger 801 can include a second receiving compartment 803 for receiving a second zirconium phosphate sorbent module or a sorbent module containing a different sorbent material, such as zirconium oxide. The sorbent recharger 801 can also include one or more pumps and valves (not shown in FIG. 6) for selectively delivering the recharging fluids from the fluid sources to the sorbent modules. As shown in FIG. 6, the recharging fluid sources are housed external to the sorbent recharger 801. Alternatively, the recharging fluid sources can be housed within the sorbent recharger 801. A drain line (not shown) can be connected to the sorbent recharger 801 for disposal of waste fluids exiting the sorbent modules. The drain line can be fluidly connected to a drain, or alternatively, the drain line can be fluidly connected to one or more waste reservoirs for storage and later disposal. As illustrated in FIG. 6, the sorbent recharger 801 can be small enough to fit on top of a table 808. However, larger sorbent rechargers can be used. A user interface 809 can allow user control of the recharging process and provide messages concerning the recharging. Door 810 controls access to the receiving compartments 802 and 803 during recharging.

Dialysis Parameter Setting Systems and Methods

Systems and methods for setting the dialysis parameters based on an analysis of the effluent obtained from a sorbent cartridge during ammonium removal are provided. The dialysis parameter setting system can have at least one dialysis parameter setting component or processor that transmits data or instructions to a dialysis machine to set or adjust dialysis parameters. A non-limiting group of dialysis parameters includes dialysate flow rate, blood flow rate, dialyzer size, amount of zirconium phosphate, sorbent module size or capacity, a bicarbonate addition profile, or combinations thereof. The system can include an identifier such as a radio-frequency identification (RFID) marker tag having data for use in a dialysis process affixed on any one or more of a dialysis machine, sorbent cartridge or module, recharger for recharging the sorbent cartridge or module, or ammonium removal system. The identifier can be a component that is capable of receiving information from an RFID tag, one-wire security component or wireless authentication component, or by scanning a bar code. The identifier can contain a RFID chip and a memory chip bonded in a smart card. The system can communicate or transfer data and/or instructions between any one of the dialysis machine, sorbent cartridge or module, recharger, or ammonium removal system. For example, the system and method can receive sensor data from a recharger or ammonium removal system, estimate a patient BUN based on the received sensor data, determine appropriate dialysis parameters, and communicate the dialysis appropriate parameter setting to a dialysis machine for use during a dialysis therapy session. Alternatively, a processor on the dialysis machine can directly process the data received from the recharger and adjust the dialysis parameter settings.

A control system in the systems and methods can determine the optimal dialysis parameter sessions based on estimated patient pre-dialysis BUN level obtained from fluid characteristics in an ammonium removal solution effluent. The obtained data can include pH for a patient based on the patient's pre-treatment urea level. Alternatively, a user interface can be provided, with the user directly inputting the desired optimal dialysis parameter sessions based on estimated patient pre-dialysis BUN level. The control system can be any component capable of monitoring and affecting the states of the dialysis machine. The control system can use processors, memory and computer components to carry out the functions described. The control system can be in communication with the pumps and valves of the dialysis machine flow paths and can control the pumps and valves in accordance with stored instructions. The control system can receive data from sensors on either the dialysis machine, recharger, or ammonium removal system, and control pumps and valves of either the dialysis machine, recharger, or ammonium removal system. The control system can automatically determine the optimal dialysis parameter settings using mathematical algorithms or look-up tables and operate the pumps and valves of the recharging flow paths to control dialysis therapy based on the estimated ammonia.

Figure 7A:
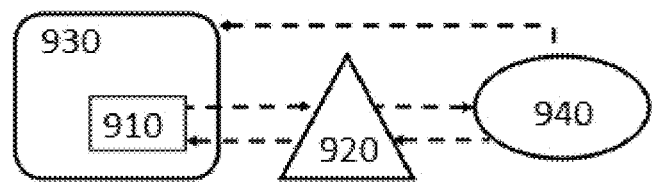
FIGS. 7A-7C show examples of a dialysis parameter setting system having at least one dialysis parameter setting component, an identifier, and a processor, where signals are being transferred within the components of the system.
Figure 7B:
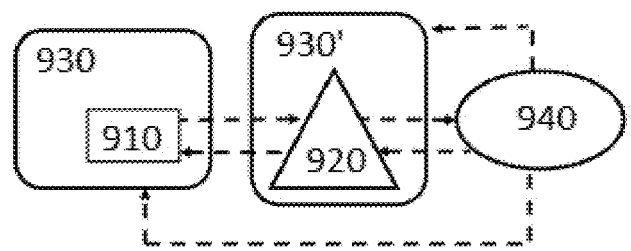
Figure 7C:
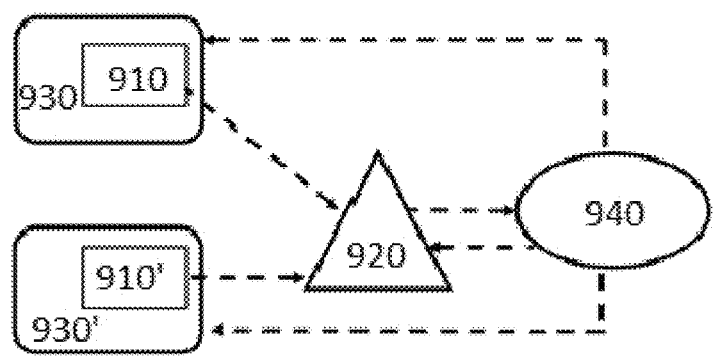

FIGS. 7A-7C show different examples of a dialysis parameter setting system. FIG. 7A shows the dialysis parameter setting system containing a dialysis parameter setting component 910, which is affixed on a dialysis component 930 to communicate with an identifier 920 through data transferring therebetween. The dialysis component 930 can be any component such as a sorbent cartridge, recharger, ammonium removal system, or dialysis machine. The identifier 920 can be affixed to the dialysis component 930 and transmit wireless or wired signals to the dialysis parameter setting component 910, read the dialysis parameter setting component 910, and further transfer the data received from the dialysis parameter setting component 910 to a processor 940 located on the dialysis component 930, connected via a local area network (LAN), or connected to remote servers as described herein.

FIG. 7B shows a dialysis parameter setting system having an identifier 920 affixed upon a second dialysis component 930' to communicate with a dialysis parameter setting component 910 of the first dialysis component 930. When the two dialysis components are assembled together or brought close to each other, data communication may occur between the identifier 920 and the dialysis parameter setting component 910. Data received by the identifier 920 can further be transferred to the processor 940. For example, a sorbent cartridge having the identifier 920 can be connected to a dialysis machine indicated by dialysis component 930.

An identifier can also transmit data between disparate components of a dialysis system such as a recharger, ammonium removal system, sorbent cartridge, or dialysis machine. FIG. 7C shows that an identifier 920 can communicate with dialysis parameter setting components 910 and 910' of different dialysis setting components 930 and 930'. Data received from the dialysis parameter setting components 910 and 910' can then be transferred to a processor 940 via the identifier 920. The processor 940 can then make determination regarding the multiple dialysis components 930 and 930', such as whether dialysis components 930 and 930' are matched with each other and transmit an estimated ammonia level in the recharger effluent. In a non-limiting example, dialysis component 930 may be a recharger and dialysis component 930' may be a sorbent cartridge having a reusable module wherein the estimate ammonia level or the obtained measurement from one or more sensors is transmitted.

Identifiers 920 can be attached to a dialysis component or be a separate device. An identifier 920 may be a multimode type reader that can communicate with at least two different types of the dialysis parameter setting component. An identifier 920 may distinguish at least two of the dialysis parameter setting components from each other, when the at least two dialysis parameter setting components are available to the identifier at the same time. An identifier 920 may also contain additional information from other sources, such as pre-stored patient information including those received previously from a different dialysis parameter setting component. The information received or stored in an identifier 920 can be further transferred to a processor 940. An identifier 920 can also receive information from the processor 940. The processor 940 can make a determination based on the received data from the identifier 920 regarding the one or more dialysis component 930. The processor 940 may be a part of the identifier 920, a part of the dialysis component 930 or any other component of the dialysis system, such as a console or a dialysis cabinet. Alternatively, the processor can be part of a stand-alone analysis system or a processor in communication with an electronic medical record system. The processor 940 may also be a device that can be connected to the dialysis system through wired or wireless communication. The determination made by the processor 940 can then be displayed on a screen (not shown) to timely notify a user. The screen may be a part of the processor 940, a part of the dialysis component 930, a part of the identifier 920, or a separate device. A user can also be notified the determination result of the processor 940 through sound signals, light signals, or any other suitable means of information delivery.

The processor 940 can correlate dialysis component-specific unique information with user-specific unique information, and correlate manufacture-specific unique identifier with dialysis component-unique information, when such information is received by the processor 940. The processor 940 can also determine other characteristics of the dialysis components, such as whether a rechargeable component is fully recharged, whether a sorbent cartridge matches the dialysis system, and whether the dialysis parameter settings of the dialysis system are proper for the patient. The processor 940 can further control the dialysis parameter settings of the dialysis system, such as blood flows, ultrafiltration rate, and ultrafiltration profile.

In non-limiting examples, activation of the dialysis parameter setting system can start from the communication between one or more identifiers 920 and one or more dialysis parameter setting components 910 in response to a particular event. The particular event may occur when a user brings close the identifiers to the dialysis parameter setting components. For example, when two dialysis components carrying the dialysis parameter setting component and the identifier, respectively, are being installed in the dialysis system. The communication between an identifier and a dialysis parameter setting component can also occur when an operation, such as a recharging process, is initiated. The activation of the dialysis parameter setting system such as an RFID system for the signals communicated or received from the RFID components can be one of the first steps in the process of recharging. The communication process between the identifier 920 and the dialysis parameter setting component 910 can also be manually initiated by a user at any stage of the communication process. In non-limiting examples, an identifier 920 may continuously communicate with the dialysis parameter setting component 910 once the communication starts. The communication may be interrupted by a user's command or may be controlled by an automatic process to stop. For example, when a reusable module is determined not suitable for a recharger, the identifier 920 may stop communicating with the dialysis parameter setting component 910.

Patient BUN Estimation

Based on an analysis of the effluent received from an ammonia sensor in the effluent line of the ammonium removal or recharging flow path, or based on the total ammonia content of collected effluent in a reservoir, the processor can integrate the total ammonia content of the ammonium removal solution effluent at each point in time during the process to determine the total amount of ammonia removed from the zirconium phosphate sorbent module, which will equal the total amount of ammonia removed by the zirconium phosphate during the previous dialysis session. The zirconium phosphate sorbent module can be flushed or back flushed with an ammonium removal solution either during recharging of the zirconium phosphate sorbent module, or with a standalone apparatus for introducing an ammonium removal solution through the zirconium phosphate sorbent module. As described, the processor can alternatively receive the total ammonia content of the ammonium removal solution effluent a single time, or at preset intervals. The total ammonia in the ammonium removal solution effluent can be determined as a volume-averaged total ammonia content in the effluent line or the total ammonia content of the collected effluent. The total ammonia removed from the zirconium phosphate sorbent module is twice the amount of urea removed by the sorbent cartridge during the dialysis session, as each molecule of urea produces two molecules of ammonia. The total amount of urea removed by the sorbent cartridge can be approximated as equal to the total amount of urea fed through the sorbent cartridge during treatment times the average conversion of urea by the urease within the sorbent cartridge, as shown in EQ(1).

$$\text{Total urea} = (\text{total ammonia})/2X \qquad \text{EQ(1)}$$

Where X is equal to the average urea conversion in the sorbent cartridge. The total urea in the dialysate during the dialysis session is given by EQ(2).

$$\text{Total urea} = Q_d * t * \overline{C}_{Durea} \qquad \text{EQ(2)}$$

Where $Q_d$ is the dialysate flow rate, t is the length of the dialysis session, and $\overline{C}_{Durea}$ is the average urea concentration in the dialysate. EQ(3) provides an alternative method for determining the amount of total urea in the dialysate during the dialysis session.

$$\text{Total urea} = V_{prp} * C_{Burea,prp} - V_{post} * C_{Burea,post} \qquad \text{EQ(3)}$$

Where $V_{prp}$ is a patient water volume prior to the dialysis session, $V_{post}$ is the patient water volume after the dialysis session, $C_{Burea,\ prp}$ is the patient blood urea level prior to the dialysis session, and $C_{Burea,\ post}$ is the patient blood urea level after the dialysis session. The patient water volume before the dialysis session can be determined via bioimpedance, or estimated based on the patient weight. In certain embodiments, the patient water volume prior to the dialysis session can be assumed as 0.58*the patient weight. After the dialysis session, the patient water volume can be determined by bioimpedance, estimated based on weight, or determined by the pre-session patient water volume minus the total ultrafiltration during the dialysis session. $C_{Burea,\ post}$ can be estimated based on the urea reduction ratio (URR), as shown in EQ(4).

$$URR = 1 - \frac{C_{Burea,\ post}}{C_{Burea,\ prp}} \text{ or } C_{Burea,post} = URR * C_{Burea,prp} \qquad \text{EQ(4)}$$

The urea reduction ratio can be estimated based on patient volume, dialyzer clearance, and session time, as shown in EQ(5).

$$URR = 1 - e^{-kt/V} \qquad \text{EQ(5)}$$

Where k is the dialyzer clearance, t is the length of time of the dialysis session, and v is the patient volume. The dialyzer clearance can be determined using EQ(5).

$$k = \frac{e^S - 1}{\frac{e^S}{Q_B} - \frac{1}{Q_d}}; S = \frac{K_o A\left(1 - \frac{Q_B}{Q_D}\right)}{Q_B} \qquad \text{EQ(6)}$$

Where $Q_B$ is the blood flow rate during the dialysis session, $Q_D$ is the dialysate flow rate during the dialysis session, and $K_o A$ is the dialyzer mass transfer coefficient, which can be obtained from a dialyzer specification sheet. Alternatively, the dialyzer clearance can be determined with online clearance monitoring, using techniques known in the art. In certain embodiments, a bolus of NaCl can be added to the dialysate, and the conductivity delta across the dialyzer can be used to estimate clearance. However, any known methods of determining the dialyzer clearance can be used.

As described, the total ammonia removed by the zirconium phosphate can be determined by EQ(7).

$$\text{Total NH}_4 = \overline{C}_{NH4,eff} * V_{eff} \qquad \text{EQ(7)}$$

Where $\overline{C}_{NH4,\,eff}$ is a volume averaged total ammonia content in the ammonium removal solution effluent as determined by an ammonia sensor, and $V_{eff}$ is the total volume of ammonium removal solution introduced through the zirconium phosphate sorbent module. As described, the total $NH_4$ can also be measured by measuring the total ammonia content of effluent collected in a reservoir or container. The total urea removed by the sorbent cartridge is given by EQ(8).

$$\text{Total urea} = \frac{\text{Total NH}_4}{2X} \qquad \text{EQ(8)}$$

Plugging the total urea equations into EQ's(1-6) and rearranging allows for estimation of the patient pre-dialysis BUN level, $C_{Burea,\,prp}$, as shown in EQ(9).

$$C_{Burea,prp} = \frac{\text{total urea}}{V_{prp} - V_{post}(1 - URR)} = \qquad \text{EQ(9)}$$

$$\frac{\text{Total NH}_4/2X}{V_{prp} - V_{post}(1 - URR)} = \frac{\overline{C}NH4,\,eff * Veff/2X}{V_{prp} - V_{post}(1 - URR)}$$

Example 1

As a non-limiting example of the patient pre-dialysis BUN estimation using a blood flow rate during a dialysis session as 0.3 L/min, a dialysate flow rate of 0.5 L/min, and a dialyzer mass transfer coefficient (KoA) of 1.1-L/min, EQ(6) provides a dialyzer clearance of 0.2679 L/min. Assuming a patient weight of 80 kg, the patient water volume prior to dialysis can be assumed as 0.58*80 kg, or 46.4 L. During a 240 minute dialysis session, the URR can be calculated as URR=URR=1-e$^{-(0.2679)(240)/46.4}$=0.750. An ultrafiltration volume during the dialysis session of 2.0 L would result in a patient post-dialysis water volume of 44.4 L.

Assuming a volume averaged total ammonia content in the effluent recharge solution of 400 mM, a total effluent recharge solution volume of 6.0 L, and an average urea conversion by the sorbent cartridge of 0.90, EQ(9) provides the patient pre-dialysis BUN estimation as $$C_{Burea,prp} = \frac{400 * 6.0/(2 * 0.9)}{46.4 - 44.4(1 - 0.75)} = 38 \text{ mM urea.}$$

One of skill in the art will understand that the values used in the example patient pre-dialysis BUN estimation are for illustrative purposes only. Actual values for actual patients will vary. However, EQ's(1-9) can be used with any starting values to provide an estimation of the patient pre-dialysis BUN level.

In certain cases, where the ammonium capacity of the zirconium phosphate is exceeded, ammonia breakthrough may occur. The dialysis system can detect ammonia breakthrough with an ammonia sensor in the dialysate flow path and can record the time of ammonia breakthrough. The patient pre-dialysis BUN level can still be estimated using EQ's(1-9) as described with a known dialysate flow rate and time of ammonia breakthrough.

One skilled in the art will understand that various combinations and/or modifications and variations can be made in the described systems and methods depending upon the specific needs for operation. Moreover, features illustrated or described as being part of an aspect of the invention may be used in the aspect of the invention, either alone or in combination, or follow a preferred arrangement of one or more of the described elements.

We claim:

1. A method comprising:
   recharging zirconium phosphate in a sorbent module with a sorbent recharger by introducing one or more recharge solutions through the sorbent module,
   wherein the one or more recharge solutions comprises at least water and a brine solution;
   measuring at least one fluid parameter of an effluent from the sorbent module during recharging of the zirconium phosphate;
   wherein the at least one fluid parameter of the effluent is measured in either an effluent line fluidly connected to the sorbent module or a reservoir fluidly connected to the effluent line; and
   setting at least one dialysis parameter for a subsequent dialysis session for a patient based on the at least one fluid parameter of the effluent,
   wherein the sorbent module was used by the patient in a previous dialysis session.

2. The method of claim 1, wherein the at least one fluid parameter of the effluent is received from a at least one sensor in the effluent line or in the reservoir fluidly connected to the effluent line.

3. The method of claim 1, wherein the at least one fluid parameter of the effluent comprises a total ammonia content in the effluent of the sorbent module; and wherein the total ammonia content in the effluent is received from an ammonia sensor.

4. The method of claim 3, further comprising:
   estimating a patient pre-dialysis blood urea nitrogen (BUN) level based on the total ammonia content of the effluent.

5. The method of claim 3, wherein the setting at least one dialysis parameter for the subsequent dialysis session comprises setting at least one of: a dialysate flow rate, a blood flow rate, a dialyzer size, a zirconium phosphate sorbent module size, a sorbent cartridge size, a bicarbonate addition profile, dialysis session timing, dialysis session time, dialysis session frequency, or combinations thereof.

6. The method of claim 5, wherein the setting at least one dialysis parameter for the subsequent dialysis session comprises reducing a dialysate flow rate, reducing a blood flow rate, reducing a dialyzer size, reducing a zirconium phosphate sorbent module size, reducing a sorbent cartridge size, increasing a bicarbonate addition profile, decreasing dialysis session frequency, or combinations thereof in response to a patient pre-dialysis BUN level below a patient pre-dialysis BUN level for a prior dialysis session.

7. The method of claim 2, wherein the at least one sensor further comprises a pH sensor or a temperature sensor.

8. The method of claim 1, wherein the method is performed by a processor of the sorbent recharger.

9. The method of claim 8, wherein the processor is programmed to receive an ammonia content of the effluent at preset intervals or continuously.

10. The method of claim 1, wherein the sorbent recharger recharges at least one sorbent material.

11. The method of claim 10, wherein the recharging restores a functional capacity of the at least one sorbent material putting the at least one sorbent material back into a condition for reuse or use in a new dialysis session.

12. A system comprising:
an ammonium removal flow path comprising:
at least one ammonium removal solution source,
wherein the ammonium removal solution source is fluidly connectable to a zirconium phosphate module inlet;
a pump; and
an effluent line fluidly connectable to a zirconium phosphate module outlet,
wherein either the effluent line comprises at least one sensor, or further comprising a reservoir fluidly connected to the effluent line,
wherein the reservoir comprises at least one sensor;
a processor in communication with the at least one sensor,
wherein the at least one sensor measures a fluid parameter during recharging of the zirconium phosphate module after a previous dialysis session for a patient;
wherein the processor sets at least one dialysis parameter for a subsequent dialysis session of the patient based on the fluid parameter; and
a sorbent recharger,
wherein the ammonium removal flow path is a zirconium phosphate recharging flow path;
wherein the at least one ammonium removal solution source comprises at least one recharge solution source,
wherein the at least one recharge solution source comprises at least a water source and a brine source.

13. The system of claim 12, wherein the at least one sensor is positioned in the effluent line.

14. The system of claim 12, wherein the at least one sensor is positioned in the reservoir fluidly connected to the effluent line.

15. The system of claim 12, wherein the at least one sensor is an ammonia sensor.

16. The system of claim 14, wherein the at least one sensor further comprises a pH sensor or a temperature sensor.

17. The system of claim 12, wherein the at least one dialysis parameter is selected from: a dialysate flow rate, a blood flow rate, a dialyzer size, a zirconium phosphate sorbent module size, a sorbent cartridge size, an amount of zirconium phosphate minimally required for therapy, a bicarbonate addition profile, dialysis session timing, dialysis session time, dialysis session frequency, or combinations thereof.

18. The system of claim 12, wherein the at least one dialysis parameter is a bicarbonate addition profile.

19. The system of claim 12, wherein the processor further estimates a patient pre-dialysis BUN level.

20. The system of claim 12, wherein the processor is programmed to receive the fluid parameter from the at least one sensor at preset intervals or continuously.

21. The system of claim 12, wherein the sorbent recharger recharges at least one sorbent material.

22. The system of claim 21, wherein recharging restores a functional capacity of the at least one sorbent material putting the at least one sorbent material back into a condition for reuse or use in a new dialysis session.

* * * * *